US011352652B2

(12) United States Patent
Takaya et al.

(10) Patent No.: US 11,352,652 B2
(45) Date of Patent: Jun. 7, 2022

(54) METHOD FOR PRODUCING 4-AMINOCINNAMIC ACID, AND VECTOR AND HOST CELL USED IN SAME

(71) Applicant: JAPAN SCIENCE AND TECHNOLOGY AGENCY, Kawaguchi (JP)

(72) Inventors: Naoki Takaya, Tsukuba (JP); Shunsuke Masuo, Tsukuba (JP); Yukie Kawasaki, Tsukuba (JP); Hajime Minakawa, Tsukuba (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 26 days.

(21) Appl. No.: 16/976,222

(22) PCT Filed: Mar. 4, 2019

(86) PCT No.: PCT/JP2019/008482
§ 371 (c)(1),
(2) Date: Aug. 27, 2020

(87) PCT Pub. No.: WO2019/168203
PCT Pub. Date: Sep. 6, 2019

(65) Prior Publication Data

US 2021/0017555 A1 Jan. 21, 2021

(30) Foreign Application Priority Data

Mar. 2, 2018 (JP) ............................ JP2018-037794

(51) Int. Cl.
*C12P 13/00* (2006.01)

(52) U.S. Cl.
CPC ............ *C12P 13/00* (2013.01); *C12P 13/001* (2013.01); *C12P 13/008* (2013.01)

(58) Field of Classification Search
None
See application file for complete search history.

(56) References Cited

U.S. PATENT DOCUMENTS

2003/0166645 A1 9/2003 Ala et al.
2014/0259212 A1 9/2014 Plesch et al.
(Continued)

FOREIGN PATENT DOCUMENTS

EP 3 103 877 A1 12/2016
EP 3121 275 A1 1/2017
(Continued)

OTHER PUBLICATIONS

Lovelock et al., "Phenylalanine ammonia lyase catalyzed synthesis of amino acids by an MIO-cofactor independent pathway", Angew. Chem. Int. Ed., vol. 53, pp. 4652-4656, 2014 (Year: 2014).*
(Continued)

*Primary Examiner* — Richard C Ekstrom
(74) *Attorney, Agent, or Firm* — Buchanan Ingersoll & Rooney PC

(57) ABSTRACT

Provided is a novel method for producing 4-aminocinnamic acid from 4-nitrophenylalanine. This method comprises: converting 4-nitrophenylalanine into 4-nitrocinnamic acid; and converting 4-nitrocinnamic acid into 4-aminocinnamic acid.

17 Claims, 10 Drawing Sheets
Specification includes a Sequence Listing.

(56) References Cited

U.S. PATENT DOCUMENTS

| | | | | |
|---|---|---|---|---|
| 2014/0323679 | A1 | 10/2014 | Kaneko et al. | |
| 2016/0362711 | A1 | 12/2016 | Konishi et al. | |
| 2017/0022528 | A1 | 1/2017 | Konishi et al. | |
| 2021/0017555 | A1 * | 1/2021 | Takaya ................. | C12N 9/0036 |

FOREIGN PATENT DOCUMENTS

| | | | |
|---|---|---|---|
| WO | 03/000255 | A1 | 1/2003 |
| WO | 2008/034648 | A1 | 3/2008 |
| WO | 2011/060920 | A2 | 5/2011 |
| WO | 2013073519 | A1 | 5/2013 |
| WO | 2015119251 | A1 | 8/2015 |
| WO | 2015141791 | A1 | 9/2015 |

OTHER PUBLICATIONS

Database DDBJ/EMBL/GenBank [online], Accession No. 049836, <https://www.ncbi.nlm.nih.gov/protein/3914262?sat=47&satkey=13492863> Jan. 31, 2018 uploaded, [retrieved on May 10, 2019] Definition: RecName: Full=Phenylalanine ammonia-lyase 2; Short=PAL-2, p. 2.

Database DDBJ/EMBL/GenBank [online], Accession No. EIW11857, <https://www.ncbi.nlm.nih.gov/protein/EIW11857> Mar. 18, 2015 uploaded, [retrieved on May 10, 2019] Definition: Frm2p [*Saccharomyces cerevisiae* CEN.PK113-7D], p. 2.

Database DDBJ/EMBL/GenBank [online], Accession No. P17117, <https://www.ncbi.nlm.nih.gov/protein/730007?sat=46&satkey=145009368> Jan. 31, 2018 uploaded, [retrieved on May 10, 2019] Definition: RecName: Full=Oxygen•insensitive NADPH nitroreductase; AltName: Full=Modulator of drug activity A, p. 5.

Database DDBJ/EMBL/GenBank [online], Accession No. P38489, <https://www.ncbi.nlm.nih.gov/protein/585554?sat=46&satkey=145008969> Jan. 31, 2018 uploaded, [retrieved on May 10, 2019] Definition: RecName: Full=Oxygen-insensitive NAD(P)H nitroreductase; AltName: Full=Dihydropteridine reductase; AltName: Full=FMN•dependent nitroreductase, p. 6.

Database DDBJ/EMBL/GenBank [online], Accession No. P45726, <https://www.ncbi.nlm.nih.gov/protein/1171998?sat=47&satkey=13492906> Jan. 31, 2018 uploaded, [retrieved on May 10, 2019] Definition: RecName: Full=Phenylalanine ammonia-lyase, p. 2.

Database DDBJ/EMBL/GenBank [online], Accession No. PBG29660, <https://www.ncbi.nlm.nih.gov/protein/PBG29660> Sep. 14, 2017 uploaded, [retrieved on May 10, 2019] Definition: NADH oxidase [Clostridioides difficile], p. 2.

Database DDBJ/EMBL/GenBank [online], Accession No. Q96VH4, <https://www.ncbi.nlm.nih.gov/protein/74644560?sat=46&satkey=145043964>, Jan. 31, 2018 uploaded, [retrieved on May 16, 2019] Definition: RecName: Full=Putative nitroreductase HBNL AltName:Full=Homologous to bacterial nitroreductases protein 1, p. 2.

Kawasaki, Y. et al., "Novel polycondensed biopolyamide generated from biomass-derived 4-aminohydrocinnamic acid", Applied Microbiology and Biotechnology, vol. 102, pp. 631-639, 2017 (month unknown).

Suvannasara, P. et al., "Biobased Polyimides from 4-Aminocinnamic Acid Photodimer", Macromolecules, pp. 1586-1593, 47(5), 2014 (month unknown).

International Search Report (PCT/ISA/210) dated May 28, 2019, by the Japan Patent Office as the International Searching Authority for International Application No. PCT/JP2019/008482, and English language translation of International Search Report.

Written Opinion (PCT/ISA/237) dated May 28, 2019, by the Japan Patent Office as the International Searching Authority for International Application No. PCT/JP2019/008482, and English language translation of Written Opinion.

Minakawa et al., "Fermentation and Purification of Microbial Monomer 4-Amminocinnamic Acid to Produce Ultra-High Performance Bioplastics", Process Biochemistry, (Nov. 30, 2018), vol. 77, pp. 100-105.

Sebaihia et al., "The Multidrug-Resistant Human Pathogen Clostridium Difficile has a Highly Mobile, Mosaic Genome", Nature Genetics, (Jul. 1, 2006), vol. 38, No. 7, pp. 779-786.

The extended European Search Report dated Nov. 12, 2021, by the European Patent Office in corresponding European Patent Application No. 19761067.8-1118. (14 pages).

* cited by examiner

FIG.1

| Enzyme | Substrate* | Specific activity mmol $min^{-1}$ $mg^{-1}$ | Km $mM^{-1}$ | Kcat $S^{-1}$ | Kcat / Km $S^{-1}$ mM |
|---|---|---|---|---|---|
| RgPAL | Phe | 0.96 | 1.29±0.17 | 22.85 | 17.71 |
| | n-Phe | 0.09 | >4.3 | N.D. | N.D. |
| CamPAL | Phe | 1.43 | 0.11±0.03 | 14.97 | 136.07 |
| | n-Phe | 1.14 | 0.62±0.11 | 23.81 | 38.40 |
| LiePAL | Phe | 1.08 | 0.11±0.02 | 4.88 | 44.35 |
| | N-Phe | 0.40 | 2.69±0.27 | 24.93 | 9.27 |

*Phe: Phenylalanine, n-Phe: 4-nitrophenylalanine

FIG.5

| Bacterial cells (g/L) | 4-nitrophenylalanine (g/L) | 4-nitrocinnamic acid (g/L) | Yield (%) |
|---|---|---|---|
| 10 | 4.2 | 3.8±0.7 | 91 |
| | 21 | 10.7±1.4 | 51 |
| | 42 | 10.9±0.7 | 26 |
| 20 | 4.2 | 2.9±0.5 | 68 |
| | 21 | 14.3±1.4 | 68 |
| | 42 | 19.0±1.4 | 45 |
| 30 | 4.2 | 2.7±0.3 | 63 |
| | 21 | 12.6±1.2 | 60 |
| | 42 | 17.3±0.8 | 41 |

METHOD FOR PRODUCING 4-AMINOCINNAMIC ACID, AND VECTOR AND HOST CELL USED IN SAME

FIELD

The present invention relates to a novel method for producing 4-aminocinnamic acid, which is useful as a raw material monomer for biomass-derived aromatic polymers, as well as to a novel vector and host cell for use in the method.

BACKGROUND

Concerns over exhaustion of petroleum resources and the issue of carbon dioxide emissions have increased the importance of systems for producing fuel and chemical products using biomass, which is a renewable resource. While examples of biomass-derived polymers include aliphatic polymers and aromatic polymers, research and development are currently progressing mainly on aliphatic polymers such as polylactic acid. Polylactic acid has been challenged by low heat resistance and durability, but this problem is being solved by, e.g., improvement in crystallinity. On the other hand, aromatic polymers often exhibit excellent material properties in terms of thermal stability and mechanical strength, and are expected to be used as raw materials for engineering plastics.

Of particular interest as a raw material monomer for biomass-derived aromatic polymers is 4-aminocinnamic acid. Patent Document 1 and Non-Patent Document 1, for example, report a method for synthesizing an aromatic polymer excellent in high heat resistance using 4-aminocinnamic acid as a raw material. Accordingly, there is a demand for a method of synthesizing 4-aminocinnamic acid from biomass with high efficiency, as a raw material monomer of such a high heat-resistance polymer.

The present inventors have developed a method for synthesizing 4-aminocinnamic acid from glucose in biomass using microbial-derived enzymes along a route wherein glucose is first converted to chorismic acid, then to 4-aminophenylpyruvate, and finally to 4-aminophenylalanine (Patent Document 2), which 4-aminophenylalanine is then converted to 4-aminocinnamic acid (Patent Document 3).

[Formula 1]

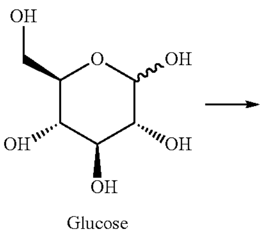

Glucose

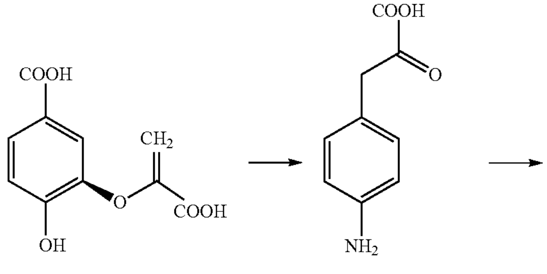

Chorismic acid 4-aminophenylpyruvic acid

-continued

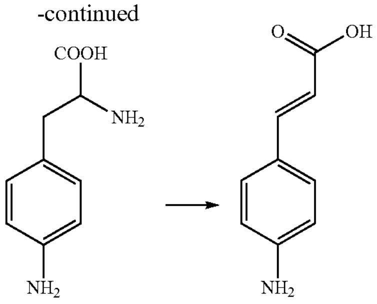

4-aminophenylalanine 4-aminocinnamic acid

CITATION LIST

Patent Documents

[Patent Document 1] WO2013/073519A
[Patent Document 2] WO2015/141791A
[Patent Document 3] WO2015/119251A

NON-PATENT DOCUMENTS

[Non-Patent Document 1] Suvannasara et al., Macromolecules, (2014), 47[5]1586-1593

SUMMARY

Technical Problem

Although the present inventors' method for synthesizing 4-aminocinnamic acid mentioned above is an excellent method, there is still room for improvement in terms of reaction rate and reaction efficiency.

An objective of the present invention is to provide a novel method for synthesizing 4-aminocinnamic acid.

Solution to Problem

The present inventors have made earnest studies and, as a result, have conceived that a novel route for synthesizing 4-aminocinnamic acid from glucose can be established by using 4-nitrophenylalanine, whose synthetic pathway from glucose is known, as a raw material, and converting it to 4-nitrocinnamic acid and then to 4-aminocinnamic acid. The present inventors have also conceived that both the conversion of 4-nitrophenylalanine to 4-nitrocinnamic acid and the conversion of 4-nitrocinnamic acid to 4-aminocinnamic acid can be achieved using appropriate enzymes of biological origins, thereby accomplishing the present invention.

Some aspects of the present invention relate to the following:

[1] A method for producing 4-aminocinnamic acid from 4-nitrophenylalanine, comprising the steps of:

(1) converting 4-nitrophenylalanine to 4-nitrocinnamic acid; and (2) converting 4-nitrocinnamic acid to 4-aminocinnamic acid.

[2] The method according to [1], wherein the conversion of step (1) is carried out by using a first enzyme which has an amino acid sequence having a sequence homology of 80% or more to an amino acid sequence shown in SEQ ID NOs:1, 3, or 5 and which has the ability to convert 4-nitrophenylalanine to 4-nitrocinnamic acid.

[3] The method according to [2], wherein the conversion of step (1) is carried out with a first host cell which has been engineered to express the first enzyme.

[4] The method according to [3], wherein the first host cell is a microorganism cell.

[5] The method according to [4], wherein the microorganism is a bacterium.

[6] The method according to [5], wherein the conversion of step (1) is carried out via a resting-cell reaction using a resting bacterial cell as the first host cell.

[7] The method according to any one of [1] to [6], wherein the conversion of step (2) is carried out by using a second enzyme which has an amino acid sequence having a sequence homology of 80% or more to an amino acid sequence shown in SEQ ID NOs:7, 9, 11, 13, or 15 and which has the ability to convert 4-nitrocinnamic acid to 4-aminocinnamic acid.

[8] The method according to [7], wherein the conversion of step (2) is carried out by using a second host cell which expresses the second enzyme.

[9] The method according to [8], wherein the second host cell is a host cell engineered to express the second enzyme.

[10] The method according to [8] or [9], wherein the second host cell is a microorganism cell.

[11] The method according to [10], wherein the microorganism is a bacterium.

[12] The method according to [11], wherein the conversion of step (2) is carried out via a resting-cell reaction using a resting bacterial cell as the second host cell.

[13] The method according to [6] or [12], wherein the resting bacterial cell is selected from the group consisting of cultured cells, powdered cells, and immobilized cells.

[14] The method according to any one of [7] to [13], wherein the conversion of step (2) is carried out at a pH of from 8 to 9.

[15] A method for producing 4-aminocinnamic acid from glucose, comprising the steps of:

(a) producing phenylalanine from glucose;

(b) converting the phenylalanine obtained in step (a) to 4-nitrophenylalanine via nitration; and (c) producing 4-aminocinnamic acid from the 4-nitrophenylalanine obtained in step (b) via a method according to any one of [1] to [14].

[16] A method for producing 4-aminocinnamic acid from phenylalanine, comprising the steps of:

(b) converting phenylalanine to 4-nitrophenylalanine via nitration; and (c) producing 4-aminocinnamic acid from the 4-nitrophenylalanine obtained in step (b) via a method according to any one of [1] to [14].

[17] A method for producing 4-nitrocinnamic acid from 4-nitrophenylalanine, comprising:

using a first enzyme which has an amino acid sequence having a sequence homology of 80% or more to an amino acid sequence shown in SEQ ID NOs:1, 3, or 5 and which has the ability to convert 4-nitrophenylalanine to 4-nitrocinnamic acid.

[18] A method for producing 4-aminocinnamic acid from 4-nitrocinnamic acid, comprising:

using a second enzyme which has an amino acid sequence having a sequence homology of 80% or more to an amino acid sequence shown in SEQ ID NOs:7, 9, 11, 13, or 15 and which has the ability to convert 4-nitrocinnamic acid to 4-aminocinnamic acid.

[19] A vector carrying a nucleic acid encoding a first enzyme which has an amino acid sequence having a sequence homology of 80% or more to an amino acid sequence shown in SEQ ID NOs:1, 3, or 5 and which has the ability to convert 4-nitrophenylalanine to 4-nitrocinnamic acid.

[20] A vector carrying a nucleic acid encoding a second enzyme which has an amino acid sequence having a sequence homology of 80% or more to an amino acid sequence shown in SEQ ID NOs:7, 9, 11, 13, or 15 and which has the ability to convert 4-nitrocinnamic acid to 4-aminocinnamic acid.

[21] A host cell engineered to express a first enzyme which has an amino acid sequence having a sequence homology of 80% or more to an amino acid sequence shown in SEQ ID NOs:1, 3, or 5 and which has the ability to convert 4-nitrophenylalanine to 4-nitrocinnamic acid.

[22] A host cell engineered to express a second enzyme which has an amino acid sequence having a sequence homology of 80% or more to an amino acid sequence shown in SEQ ID NOs:7, 9, 11, 13, or 15 and which has the ability to convert 4-nitrocinnamic acid to 4-aminocinnamic acid.

Advantageous Effects of Invention

The present invention provides a novel method for synthesizing 4-aminocinnamic acid from glucose.

BRIEF DESCRIPTION OF DRAWINGS

FIG. 1 is a table indicating the enzymatic activities of CamPAL, LiePAL, and RgPAL, which were produced by genetically modified *E. coli* and then purified, to deammoniate phenylalanine (Phe) and 4-nitrophenylalanine (n-Phe);

FIG. 5 is a table indicating the conversion activities from 4-nitrophenylalanine to 4-nitrocinnamic acid with different amounts of bacterial cells and different amounts of the substrate;

DESCRIPTION OF EMBODIMENTS

Figure 2:
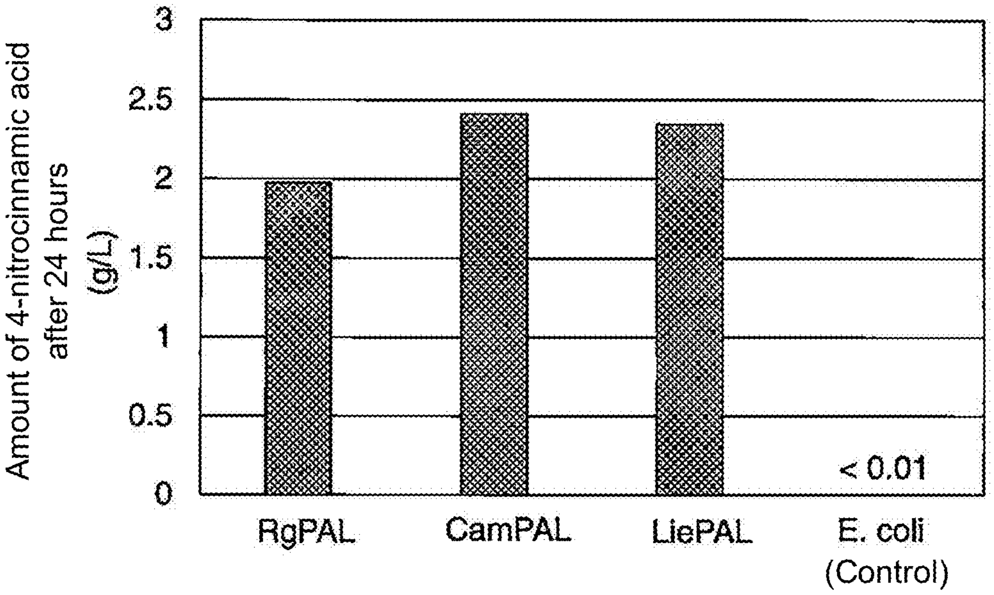
FIG. 2 is a graph showing the activities of CamPAL, LiePAL, and RgPAL, which were produced by genetically modified *E. coli* and then subjected to a resting-cell reaction, to convert 4-nitrophenylalanine to 4-nitrocinnamic acid.

The present invention will now be described in detail with reference to specific embodiments. However, the present invention is not limited to the following embodiments and can be implemented in any form without departing from the spirit of the present invention.

The term "nucleic acid" as used herein includes ribonucleic acid, deoxyribonucleic acid, and modified forms of any nucleic acids. Further, the nucleic acids include both single-stranded ones and double-stranded ones. The nucleic acid (gene) according to the present invention can be prepared by any method known to those skilled in the art, using a public organization database known to those skilled in the art and/or a primer or a probe prepared based on the nucleotide sequence disclosed in the present specification. For example, the nucleic acid according to the present invention can be easily obtained as a cDNA of the gene by using various PCR and other DNA amplification techniques known to those skilled in the art. Alternatively, the nucleic acid according to the present invention can be appropriately synthesized by those skilled in the art based on the sequence information disclosed in the present specification, using an existing technique. A nucleic acid (gene) may encode a protein or a polypeptide. The term "encode" as used herein means to express the protein or polypeptide according to the present invention in a state of exhibiting its activity. The term "encode" includes both encoding the protein according to the present invention as one or more continuous structural sequences (exons) and encoding the protein with appropriate intervening sequences (introns).

[I. Method of Producing 4-Aminocinnamic Acid from 4-Nitrophenylalanine]

1. Overview

A first aspect of the present invention relates to a method for producing 4-aminocinnamic acid from 4-nitrophenylalanine (hereinafter also referred to as "first method of the present invention"). The first method of the present invention includes at least: (1) converting 4-nitrophenylalanine to 4-nitrocinnamic acid; and (2) converting 4-nitrocinnamic acid to 4-aminocinnamic acid.

Both a process for synthesizing phenylalanine from glucose by fermentation (see, e.g., US2001/0044139A: hereinafter also referred to as "Document A") and a process for nitrating phenylalanine to synthesize 4-nitrophenylalanine (see, e.g., Takayama et al., BCSJ, 17[3]:109-113: hereinafter also referred to as "Document B") were already known.

On the other hand, the present inventors have conceived of using 4-nitrophenylalanine as a starting material, and arrived at the idea of first converting it to 4-nitrocinnamic acid and then to 4-aminocinnamic acid. Based on this idea, the present inventors have finally succeeded in establishing a new synthetic route of 4-aminocinnamic acid by starting from glucose and passing through phenylalanine, 4-nitrophenylalanine, and 4-nitrocinnamic acid in sequence.

[Formula 2]

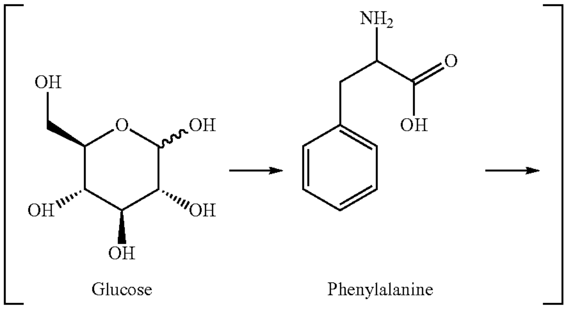

Glucose Phenylalanine

-continued

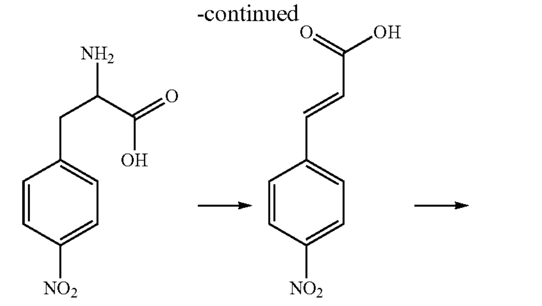

4-nitrophenylalanine 4-nitrocinnamic acid 4-aminocinnamic acid

Each of the two steps included in the first method of the present invention may be achieved by any method, such as a biological method or a chemical method.

In investigating the method for converting 4-nitrophenylalanine to 4-nitrocinnamic acid, the present inventors have screened a wide range of enzymes of biological origin for an enzyme that can convert 4-nitrophenylalanine to 4-nitrocinnamic acid (phenylalanine ammonia-lyase) and, as a result, have identified CamPAL (an enzyme derived from *Camellia sinensis*), LiePAL (an enzyme derived from *Lithospermum erythrorhizon*), and RgPAL (an enzyme derived from *Rhodotorula glutinis* JN-1).

Conversion from 4-nitrocinnamic acid to 4-aminocinnamic acid can be achieved via a reduction reaction of a nitro group using a known chemical method. Nevertheless, the present inventors have carried out screening for an enzyme which can convert 4-nitrocinnamic acid to 4-aminocinnamic acid (nitroreductase) and, as a result, have identified scFrm2 and scHbn1 (enzymes derived from *Saccharomyces cerevisiae*), cdFLDZ (an enzyme derived from *Clostridium difficile*), and nfsA and nfsB (enzymes derived from *Escherichia coli*).

Furthermore, the present inventors have succeeded in converting 4-nitrophenylalanine to 4-nitrocinnamic acid and then to 4-aminocinnamic acid using host cells expressing these enzymes, thereby having finally completed the first method of the present invention.

The first method of the present invention can be combined with the above-mentioned known methods, i.e., the method for synthesizing phenylalanine by fermentation of glucose (Document A above) and a method for synthesizing 4-nitrophenylalanine by nitration of phenylalanine (Document B above), whereby it becomes possible to produce 4-aminocinnamic acid via a new synthetic route, starting from glucose and passing through phenylalanine, 4-nitrophenylalanine, and 4-nitrocinnamic acid in sequence. In addition, as demonstrated in the Examples described below, the synthesis of 4-aminocinnamic acid from glucose via the first method of the present invention is superior to the conventional methods according to the present inventors (Patent Documents 2 and 3 above) in terms of reaction rate and reaction efficiency, and is therefore advantageous.

Hereinafter, the first method of the present invention will be described in detail.

2. Starting Material: 4-Nitrophenylalanine

The starting material used in the first method of the present invention is 4-nitrophenylalanine. The source of 4-nitrophenylalanine is not limited; it may be either natural or synthetic. Various techniques for synthesizing 4-nitrophenylalanine will be described below.

3. Step (1): Conversion of 4-Nitrophenylalanine to 4-Nitrocinnamic Acid

In the first method of the present invention, 4-nitrophenylalanine is first converted to 4-nitrocinnamic acid in step (1). The method for carrying out this step (1) is not limited, and may be achieved by any method such as a biological method or a chemical method. Among them, in the present invention, step (1) may preferably be carried out using an enzyme that converts 4-nitrophenylalanine to 4-nitrocinnamic acid (nitrophenylalanine ammonia-lyase: hereinafter also referred to as "first enzyme").

Examples of the first enzyme include: CamPAL (an enzyme derived from *Camellia sinensis*), LiePAL (an enzyme derived from *Lithospermum erythrorhizon*), and RgPAL (an enzyme derived from yeast *Rhodotorula glutinis* JN-1). The amino acid sequence of the CamPAL protein is shown in SEQ ID NO: 1, and an example of the nucleotide sequence of the CamPAL gene encoding the same (codon-optimized for best expression in *E. coli*) is shown in SEQ ID NO: 2, respectively. The amino acid sequence of the LiePAL protein is shown in SEQ ID NO:3, and an example of the nucleotide sequence of the LiePAL gene encoding the same (codon-optimized for best expression in *E. coli*) is shown in SEQ ID NO:4. The amino acid sequence of the RgPAL protein is shown in SEQ ID NO: 5, and an example of the nucleotide sequence of the RgPAL gene encoding the same (codon-optimized for best expression in *E. coli*) is shown in SEQ ID NO: 6, respectively.

CamPAL, LiePAL, and RgPAL are enzymes found by the present inventors via screening of known phenylalanine ammonia-lyases (PALs) of biological origin, as shown in the Examples described later. PAL is an enzyme that uses phenylalanine as a substrate and deammoniates it to produce cinnamic acid. There is some similarity between the conventional PAL-mediated reaction for producing cinnamic acid via deammoniation of phenylalanine and the reaction for producing 4-nitrocinnamic acid via deammoniation of 4-nitrophenylalanine, but they are different in that the substrate used in the latter reaction has a nitro group at the 4-position of the benzene ring. Unexpectedly, CamPAL, LiePAL, and RgPAL have excellent conversion activity from 4-nitrophenylalanine to 4-nitrocinnamic acid, as demonstrated in the Examples described later, and therefore can preferably be used in the present invention.

As mentioned above, CamPAL, LiePAL, and RgPAL are known enzymes, and their amino acid sequences are also known. However, these can utilize nitro compounds as substrates, and convert 4-nitrophenylalanine to 4-nitrocinnamic acid. It has not been known so far that it has the converting activity, and it is the first finding of the present inventors. However, it has not been known so far that these enzymes can utilize a nitro compound as a substrate and have the capacity to convert 4-nitrophenylalanine to 4-nitrocinnamic acid. Thus, this is a novel finding first discovered by the present inventors.

Examples of the first enzyme are not limited to CamPAL, LiePAL, and RgPAL, but also include their analogs that are polypeptides retaining the activity of converting 4-nitrophenylalanine to 4-nitrocinnamic acid. Examples of the CamPAL, LiePAL, and RgPAL analogs include their homologues (including orthologs and paralogs) and their fragments.

Specifically, the first enzyme may preferably have at least 80%, preferably at least 85%, or at least 90%, at least 95%, at least 96%, at least 97% at least 98%, particularly preferably at least 99%, and most preferably 100%, sequence homology with the amino acid sequence shown in SEQ ID NO: 1, 3, or 5. The first enzyme may also preferably have at least 80%, preferably at least 85%, or at least 90%, at least 95%, at least 96%, at least 97% at least 98%, particularly preferably at least 99%, and most preferably 100%, sequence identity with the amino acid sequence shown in SEQ ID NO: 1, 3, or 5.

The "homology" of two amino acid sequences herein means a ratio in which identical or similar amino acid residues appear at each corresponding position when the two amino acid sequences are aligned. The "identity" of two amino acid sequences herein means a ratio in which identical amino acid residues appear at each corresponding position when the two amino acid sequences are aligned. The "homology" and "identity" of two amino acid sequences can be calculated using, e.g., BLAST (Basic Local Alignment Search Tool) program (Altschul et al., J. Mol. Biol., (1990), 215(3): 403-10).

The first enzyme may also be a polypeptide having an amino acid sequence derived from SEQ ID NO: 1, 3 or 5 via deletion(s), substitution(s), or deletion(s) of one or several amino acids. The statement "deletion(s), substitution(s), or deletion(s) of one or several amino acids" herein means that amino acid(s) in the amino acid sequence have been modified without significantly affecting the structure or function of the polypeptide. The term "several" herein means that there are generally 2 to 50 mutations, preferably 2 to 20 mutations, more preferably 2 to 10 mutations, and further preferably 2 to 5 mutations (deletions, substitutions or additions).

The first enzyme may also be a polypeptide encoded by a nucleic acid that hybridizes under stringent conditions with a nucleic acid having a nucleotide sequence complementary to the nucleotide sequence encoding the amino acid sequence shown in SEQ ID NO: 1, 3, or 5. The term "stringent conditions" herein means conditions that allow selective and detectable specific binding between nucleic acids, and are defined by an appropriate combination of conditions, such as salt concentration, solvent (e.g., organic solvent such as formamide), temperature, and other known conditions. The "stringent conditions" are well-known to those skilled in the art, and are explained in, e.g., T. Maniatis et al., Ed., Molecular Cloning: A Laboratory Manual 2nd ed. (1989) Cold Spring Harbor Laboratory. Specific examples of "stringent conditions" areas follows. Hybridization is carried out according to a standard Southern blotting method, at about 40 to 45° C., optimally about 42° C., in 5×SSPE, 0.3% SDS, 200 μg/mL shear-denatured salmon sperm DNA, for 12-24 hours with: 25% formamide for very low and low stringencies; 35% formamide for medium and medium-to-high stringencies; and 50% formamide for high and very high stringencies. The carrier is then washed in 2×SSC, 0.2% SDS for 15 minutes three times at: 45° C. (very low stringency), 50° C. (low stringency), 55° C. (moderate stringency), 60° C. (moderate-to-high stringency), 65° C. (high stringency), or 70° C. (very high stringency). Hybridization can be carried out according to a method known in the art or a method analogous thereto. Alternatively, when a commercially available library is used, hybridization can be carried out according to the method described in the instruction manual attached to the library.

The method for preparing the first enzyme is not limited. For example, it may be extracted from an organism producing the first enzyme for the intended use. Alternatively, it can be prepared based on the nucleotide sequence of the CamPAL, LiePAL, or RgPAL gene, which is registered in the database of a public institute known to those skilled in the art and also disclosed herein (SEQ ID NOs: 2, 4 and 6, respectively), using various methods known to those skilled in the art, such as chemical synthesis methods and genetic engineering methods.

Specifically, CamPAL, LiePAL, or RgPAL can be prepared as follows. A nucleic acid encoding the CamPAL, LiePAL, or RgPAL gene is first prepared based on a genomic library of, for example, *Camellia sinensis, Lithospermum erythrorhizon*), or *Rhodotorula glutinis* JN-1, using a nucleic acid amplification technique known to those skilled in the art, such as a polymerase chain reaction (PCR). This nucleic acid is then incorporated to any of a variety of vectors, such as plasmids and viruses, by a method known to those skilled in the art, and the vector is introduced to an appropriate host cell by gene recombination for expression. The host cell may be either a prokaryotic cell or a eukaryotic cell; the prokaryotic cell may be derived from either a eubacterium or an archaea; and the eukaryotic cell may be a plant cell, an animal cell, a fungal cell or a protozoan cell.

An analogue of CamPAL, LiePAL, or RgPAL can be prepared as follows. A nucleic acid encoding the CamPAL, LiePAL, or RgPAL gene is first prepared based on the nucleotide sequence registered in the database of a public institute known to those skilled in the art and also disclosed herein (SEQ ID NOs: 2, 4 and 6, respectively). A nucleic acid encoding the CamPAL, LiePAL, or RgPAL analogue is then prepared by introducing one or more mutations to the nucleic acid encoding the CamPAL, LiePAL, or RgPAL gene by a method such as: contacting the nucleic acid with a drug serving as a mutagen; irradiating the nucleic acid with ultraviolet rays; or manipulating the nucleic acid using genetic engineering methods, of which site-directed mutagenesis is particularly useful since it can introduce a specific mutation at a specific position. The nucleic acid encoding the CamPAL, LiePAL, or RgPAL analog is then incorporated to any of a variety of vectors, such as plasmids and viruses, by a method known to those skilled in the art in the same manner as described above, and then introduced to an appropriate host cell using gene recombination technique for expression of the CamPAL, LiePAL, or RgPAL analog.

For genetic engineering methods, reference can be made to, e.g., Sambrook, J. et al., Molecular Cloning: A Laboratory Manual, 2nd Ed., Cold Spring Harbor Laboratory Press, Cold Spring Harbor, N.Y., 1989.

The method for carrying out step (1) using the first enzyme is not particularly limited, as long as the first enzyme is allowed to act on 4-nitrophenylalanine under conditions that cause an enzymatic reaction to convert 4-nitrophenylalanine to 4-nitrocinnamic acid. 4-nitrophenylalanine may be used in any form. For example, a composition containing 4-nitrophenylalanin, such as a natural product or a synthetic product, may be used without purification, or 4-nitrophenylalanine may be purified from such a composition by various methods known to those skilled in the art before use.

As a method for allowing the first enzyme to act on 4-nitrophenylalanine include: the first enzyme prepared by the above procedure may be isolated and purified before use, or a recombinant cell obtained by engineering a host cell to express the first enzyme (hereinafter also referred to as the "first cell") may be used as such. In the latter case, a particularly preferred method includes using resting cells of bacteria as host cells and placing them in the presence of 4-nitrophenylalanine such that the first enzyme contained in the resting cells is allowed to act on 4-nitrophenylalanine and convert it to 4-nitrocinnamic acid. This method (hereinafter also referred to as the "resting-cell reaction") will be described later.

An alternative method which can be used herein includes: using bacterial cells as host cells that express the first enzyme, combining the culture solution thereof with 4-nitrophenylalanine such that the first enzyme contained in the culture solution is allowed to act on 4-nitrophenylalanine and convert it to 4-nitrocinnamic acid.

The conditions that cause the enzymatic reaction of the first enzyme are not limited, but are as follows. In the case of an aqueous solvent, the pH may be, although not particularly limited thereto, generally 7.5 or higher, preferably 8 or higher, and generally 9.5 or lower, preferably 9 or lower. The temperature at which the reaction is carried out may be, although not particularly limited thereto, usually at 27° C. or higher, preferably 30° C. or higher, more preferably 32° C. or higher, and usually 42° C. or lower, preferably 37° C. or lower.

4. Step (2): Conversion of 4-Nitrocinnamic Acid to 4-Aminocinnamic Acid

In the first method of the present invention, 4-nitrocinnamic acid is then converted to 4-aminocinnamic acid in step (2). The method for carrying out this step (2) is not limited, and any method such as a biological method or a chemical method can be used. Among them, in the present invention, step (2) may preferably be carried out using an enzyme that converts 4-nitrocinnamic acid to 4-aminocinnamic acid (nitroreductase: hereinafter also referred to as "second enzyme").

Examples of the second enzyme include: scFrm2 and scHbn1 (enzymes derived from *Saccharomyces cerevisiae*); cdFLDZ (enzymes derived from *Clostridium difficile*); and nfsA and nfsB (enzymes derived from *Escherichia coli*). The amino acid sequence of the scFrm2 protein is shown in SEQ ID NO:7, and an example of the nucleotide sequence of the scFrm2 gene encoding it is shown in SEQ ID NO:8. The amino acid sequence of the scHbn1 protein is shown in SEQ ID NO:9, and an example of the nucleotide sequence of the scHbn1 gene encoding this is shown in SEQ ID NO:10. The amino acid sequence of the cdFLDZ protein is shown in SEQ ID NO: 11, and an example of the nucleotide sequence of the cdFLDZ gene encoding this is shown in SEQ ID NO: 12. The amino acid sequence of the nfsA protein is shown in SEQ ID NO: 13, and an example of the nucleotide sequence of the nfsA gene encoding it is shown in SEQ ID NO: 14. The amino acid sequence of the nfsB protein is shown in SEQ ID NO:15, and an example of the nucleotide sequence of the nfsB gene encoding this is shown in SEQ ID NO:16.

As shown in the Examples described later, scFrm2, scHbn1, cdFLDZ, nfsA, and nfsB are enzymes found by the present inventors via screening of known nitroreductases and enoate reductases of biological origin. Unexpectedly, these enzymes have an excellent conversion activity from 4-nitrocinnamic acid to 4-aminocinnamic acid, as shown in the Examples below, and therefore can preferably be used in the present invention.

As described above, scFrm2, scHbn1, cdFLDZ, nfsA and nfsB are enzymes known as nitroreductases or enoate reductases, and their amino acid sequences were also known. However, it has not been known so far that these enzymes can be used as nitroreductases. Thus, this is a novel finding first discovered by the present inventors.

Examples of the second enzyme are not limited to these specific enzymes, but also include their analogs that are polypeptides retaining the activity of converting 4-nitrocinnamic acid to 4-aminocinnamic acid. Examples of such analogs include their homologues (including orthologs and paralogs) and their fragments.

Specifically, the second enzyme may preferably have at least 80%, preferably at least 85%, or at least 90%, at least 95%, at least 96%, at least 97% at least 98%, particularly preferably at least 99%, and most preferably 100%, sequence homology with the amino acid sequence shown in SEQ ID NO: 7, 9, 11, 13, or 15. The second enzyme may also preferably have at least 80%, preferably at least 85%, or at least 90%, at least 95%, at least 96%, at least 97% at least 98%, particularly preferably at least 99%, and most preferably 100%, sequence identity with the amino acid sequence shown in SEQ ID NO: 7, 9, 11, 13, or 15. The meanings of the terms "homology" and "identity" of two amino acid sequences herein are as defined above.

The second enzyme may also be a polypeptide having an amino acid sequence derived from SEQ ID NO: 7, 9, 11, 13, or 15 via deletion(s), substitution(s), or deletion(s) of one or several amino acids. The meaning of the statement "deletion(s), substitution(s), or deletion(s) of one or several amino acids" herein is as defined above.

The second enzyme may also be a polypeptide encoded by a nucleic acid that hybridizes under stringent conditions with a nucleic acid having a nucleotide sequence complementary to the nucleotide sequence encoding the amino acid sequence shown in SEQ ID NO: 7, 9, 11, 13, or 15. The meaning of the term "stringent conditions" herein is as defined above.

The method for preparing the second enzyme is not limited. For example, it may be extracted from an organism producing the second enzyme for the intended use. Alternatively, it can be prepared based on the nucleotide sequence of the gene of the second enzyme, which is registered in the database of a public institute known to those skilled in the art and also disclosed herein (SEQ ID NOs: 8, 10, 12, 14, and 16, respectively), using various methods known to those skilled in the art, such as chemical synthesis methods and genetic engineering methods. The details of these methods, especially the genetic engineering methods, are as described in details above.

The method for carrying out step (2) using the second enzyme is not particularly limited, as long as the first enzyme is allowed to act on 4-nitrocinnamic acid under conditions that cause an enzymatic reaction to convert 4-nitrocinnamic acid obtained in step (1) to 4-aminocinnamic acid. 4-nitrocinnamic acid obtained in step (1) may be used in any form. For example, the reaction product of step (1) containing 4-nitrocinnamic acid may be used without purification, or 4-nitrocinnamic acid may be purified from such a composition by various methods known to those skilled in the art before use.

As a method for allowing the second enzyme to act on 4-nitrocinnamic acid include: the second enzyme prepared by the above procedure (scFrm2, scHbn1, cdFLDZ, nfsA, or nfsB, or an analog thereof) may be isolated and purified before use, or a recombinant cell obtained by engineering a host cell to express the second enzyme (hereinafter also referred to as the "second cell") may be used as such. In the latter case, a particularly preferred method includes using resting cells of bacteria as host cells and placing them in the presence of 4-nitrophenylalanine such that the first enzyme contained in the resting cells is allowed to act on 4-nitrophenylalanine and convert it to 4-aminocinnamic acid (resting-cell reaction). This method of resting-cell reaction will be described later. An preferred alternative method includes using bacterial cells as host cells that express the first enzyme, combining the culture solution thereof with 4-nitrophenylalanine such that the first enzyme contained in the culture solution is allowed to act on 4-nitrocinnamic acid and convert it to 4-aminocinnamic acid. In this case, *Escherichia coli* is preferable as the bacterium.

The conditions that cause the enzymatic reaction of the second enzyme are not limited, but may be as follows. In the case of an aqueous solvent, the pH may be, although not particularly limited thereto, generally 6.5 or higher, preferably 7.0 or higher, and generally 8.5 or lower, preferably 8.0 or lower. The temperature at which the reaction is carried out may be, although not particularly limited thereto, usually at 27° C. or higher, preferably 30° C. or higher, more preferably 32° C. or higher, and usually 42° C. or lower, preferably 37° C. or lower.

5. Resting Cell Reaction

When carrying out step (1) using the first enzyme and/or step (2) using the second enzyme in the first method of the present invention, it is preferred to carry out a reaction using resting bacterial cells (resting-cell reaction) as the first and/or second cells expressing the first and/or second enzyme(s) (hereinafter, the bacterium expressing the first enzyme is referred to as the "first bacterium," and the bacterium expressing the second enzyme is referred to as the "second bacterium.").

The term "resting bacterial cells" herein means bacterial cells that do not grow. Examples of resting bacterial cells include cultured bacterial cells obtained by culturing a bacterium, powdered bacterial cells obtained by freeze-drying or spray-drying cultured bacterial cells, and immobilized bacterial cells obtained by immobilizing cultured bacterial cells on a carrier. Two or more of these types of cells may also be used in combination. A specific example of the resting cells is a suspension of resting bacterial cells, which can be prepared by culturing a bacterium, separating the culture solution to culture supernatant and bacterial cells by centrifugation, washing the obtained bacterial cells with physiological saline, and suspending the washed bacterial cells in sterilized pure water such that the cell turbidity becomes a desired value (e.g., such that the absorbance at 600 nm becomes 40). Other examples of resting bacterial cells that can be used include: powdered bacterial cells, which are obtained by lyophilizing or spray-drying the suspension of resting bacterial cells, or immobilized bacterial cells, which are prepared by immobilizing the cultured bacterial cells in the suspension on a carrier.

The resting cells of the first or second bacterium are placed in the presence of a corresponding substrate (4-nitrophenylalanine for the first bacterium, 4-nitrocinnamic acid for the second bacterium) or a composition containing the same (for example, natural product, reaction product, etc.) under conditions that cause an enzymatic reaction of the first or second enzyme, whereby the first or second enzyme contained in the resting cells of the first or second bacterium acts on the corresponding substrate. Preferred conditions for causing the enzymatic reaction of the first or second enzyme may be, although not limited thereto, conditions in an aqueous solvent with a pH of usually 6.5 or higher, preferably 7 or higher, and usually 9.5 or lower, preferably 9 or lower, and at a temperature of usually 27° C.

or higher, especially 30° C. or higher, further 32° C. or higher, and usually 42° C. or lower, especially 37° C. or lower.

A chemical method can be used as a method for converting 4-nitrocinnamic acid to 4-aminocinnamic acid in step (2) of the first method of the present invention. The chemical method is not particularly limited, and may be any known methods. A specific example of the chemical method includes reducing the nitro group of 4-nitrocinnamic acid via a chemical reaction for converting a nitro group to an amino group. The method for reducing the nitro group is not particularly limited, but may be any known methods, such as Bechamp method (see, e.g., AJ Ann. Chim. Phys. 1854, 42, 186) and heterogeneous catalytic reduction. For this method, 4-nitrocinnamic acid obtained in step (1) above may be used as such, or may be purified by a known method as appropriate before use.

6. Others

According to the above procedure, 4-aminocinnamic acid can be produced from nitrophenylalanine by (1) converting 4-nitrophenylalanine to 4-nitrocinnamic acid and then (2) converting 4-nitrocinnamic acid to 4-aminocinnamic acid. After step (2), 4-aminocinnamic acid may be isolated and purified from the reaction product by various methods known to those skilled in the art.

It should be noted that the above description is merely one embodiment of carrying out the first method of the present invention. Those skilled in the art can easily understand that the first method of the present invention can be implemented with making modifications to the above-described embodiment as appropriate.

For example, the first method of the present invention can be carried out by combining step (1) and step (2) in any manner as appropriate. Although such a combination is not limited, a typical example is that the enzymatic reaction using the first enzyme is carried out as step (1), while the enzymatic reaction using the second enzyme or the above chemical method is carried out as step (2). The reaction in step (1) may preferably be an enzyme reaction in the presence of the first bacterium or a resting-cell reaction using the first bacterium.

When the reaction in step (1) is carried out as an enzyme reaction in the presence of the first bacterium, the reaction in step (2) may preferably be carried out either as an enzyme reaction in the presence of the second bacterium or as a chemical method. The enzyme reaction in the presence of the second bacterium is more preferred, since the enzyme reactions in steps (1) and (2) can be carried out continuously, which is advantageous in terms of efficiency. In this case, use of *Escherichia coli* as the second bacterium is even more advantageous from the viewpoint of cost reduction.

On the other hand, when the reaction in step (1) is carried out using resting cells of the first bacterium, the reaction in step (2) may preferably be carried out either as a resting-cell reaction using resting cells of the second bacterium or as a chemical method. The chemical method is more preferred in terms of conversion efficiency of 4-nitrocinnamic acid to 4-aminocinnamic acid, production cost (raw material cost, capital investment cost, labor cost, etc.), and $CO_2$ reduction during production.

Although the above description was focused on an embodiment in which step (1) is completed before step (2) is started, it is also possible to carry out step (1) and step (2) at the same time. In this case, the first and second enzymes are allowed to act on 4-nitrophenylalanine under conditions that cause the conversion of 4-nitrophenylalanine to 4-nitrocinnamic acid by the first enzyme and the conversion of 4-nitrocinnamic acid to 4-aminocinnamic acid by the second enzyme in parallel. In this case, the isolated and purified first and second enzymes may be used in combination, or the first and second cells expressing the first and second enzymes, respectively, may be used in combination. Alternatively, a single transgenic cell that expresses both the first and second enzymes (hereinafter referred to as "third cell") may be used. The third cell expressing both the first and second enzymes can be obtained by engineering a single host cell via introduction of the genes encoding the first and second enzymes, or the first and second vectors carrying these genes, respectively, such that the cell expresses both the first and second enzymes.

[II. Method for Producing 4-Aminocinnamic Acid from Glucose]

A second aspect of the present invention relates to a method of producing 4-aminocinnamic acid from glucose (hereinafter also referred to as "the second method of the present invention"). The second method of the present invention at least includes the steps of: (a) producing phenylalanine from glucose; (b) converting the phenylalanine obtained in (a) to 4-nitrophenylalanine via nitration; and (c) producing 4-aminocinnamic acid from the 4-nitrophenylalanine obtained in step (b) by the first method of the present invention.

The method of synthesizing phenylalanine from glucose in step (a) may be, e.g., the method described in Document A mentioned above.

The method of synthesizing 4-nitrophenylalanine from phenylalanine in step (b) may be, e.g., the method described in Document B mentioned above.

The method for synthesizing 4-aminocinnamic acid from 4-nitrophenylalanine in step (c) may be, e.g., the first method of the present invention explained above.

[III. Method of Producing 4-Aminocinnamic Acid from Phenylalanine]

A third aspect of the present invention relates to a method of producing 4-aminocinnamic acid from phenylalanine (hereinafter also referred to as "the third method of the present invention"). The third method of the present invention at least includes the steps of: (b) converting phenylalanine to 4-nitrophenylalanine via nitration; and (c) producing 4-aminocinnamic acid from the 4-nitrophenylalanine obtained in step (b) by the first method of the present invention.

The method of synthesizing 4-nitrophenylalanine from phenylalanine in step (b) is as explained above in relation to the second method of the present invention.

The method for synthesizing 4-aminocinnamic acid from 4-nitrophenylalanine in step (c) may be, e.g., the first method of the present invention explained above.

[IV. Method of Producing 4-Nitrocinnamic Acid from 4-Nitrophenylalanine]

A fourth aspect of the present invention relates to a method of producing 4-nitrocinnamic acid from phenylalanine (hereinafter also referred to as "the fourth method of the present invention"). The fourth method of the present invention at least includes the step of converting phenylalanine to 4-nitrocinnamic acid using the first enzyme explained above. The details of this step are as explained above as step (1) of the first method of the present invention.

[V. Method of Producing 4-Aminocinnamic Acid from 4-Nitrocinnamic Acid]

A fifth aspect of the present invention relates to a method of producing 4-aminocinnamic acid from 4-nitrocinnamic acid (hereinafter also referred to as "the fifth method of the present invention"). The fifth method of the present invention at least includes the step of converting 4-nitrocinnamic acid to 4-aminocinnamic acid using the second enzyme explained above. The details of this step are as explained above as step (2) of the first method of the present invention.

[VI. Vectors]

A sixth aspect of the present invention relates to a vector carrying a gene encoding the first and/or second enzyme(s) (hereinafter, a vector carrying a gene encoding the first enzyme is referred to as the "first vector," a vector carrying a gene encoding the second enzyme as the "second vector," and a vector carrying both a gene encoding the first enzyme and a gene encoding the second enzyme as the "third vector.").

The types of the first to third vectors are not limited as long as they are capable of carrying the gene(s) encoding the first and/or second enzyme(s) and introducing the gene(s) to a host cell such that the gene(s) can be expressed. For example, these vectors may be either those that are integrated to the genome of the host cell, or those that are incorporated to the cytoplasm of the host cell and coexist independently of the genome of the host cell, and autonomously replicate according to cell division of the host cell. They may also be linear or circular, may be single-stranded or double-stranded, and may be DNA or RNA. They may further be plasmid vectors, cosmid vectors, fosmid vectors, viral vectors, artificial chromosome vectors, bacterial vectors such as Agrobacterium, or binary vectors formed by combining two or more thereof. The type, structure, production method, etc., of such a vector are well known to those skilled in the art, and may be appropriately selected depending on various conditions such as the genes, the host cells, and the like.

In addition to the gene(s) encoding the first and/or second enzyme(s) described above, the first to third vectors may preferably further include one or more regulatory sequences that regulate expression of the gene in the host cell. Examples of such regulatory sequences include promoters, terminators, enhancers, poly-A addition signals, 5'-UTRs (untranslated regions), marker or selectable marker genes, multiple cloning sites, replication origins, and the like. In the first to third vectors, these regulatory sequences may preferably be operably linked to the gene(s) encoding the first and/or second enzyme(s) and constructed as an expression cassette, such that the gene(s) are autonomously expressed in the host cell. The type, structure, production method, etc., of such a regulatory sequence are well known to those skilled in the art, and may be appropriately selected depending on various conditions such as the genes, the host cells, and the like.

[VII. Cells]

A seventh aspect of the present invention relates to a cell obtained by engineering a host cell such that it expresses the first and/or second enzyme(s) (hereinafter, a cell expressing the first enzyme is referred to as the "first cell," a cell expressing the second enzyme as the "second cell," and a cell expressing the first and second enzymes as the "third cell.")

The type of host cells from which the first to third cells are derived is not limited, and may be prokaryotic cells or eukaryotic cells. The prokaryotic cells may be eubacterial cells or archaeal cells, and the eukaryotic cells may be plant cells, animal cells, fungal cells or protozoan cells. However, it is preferable to use bacterial cells as the host cells for carrying out the resting-cell reaction mentioned-above.

The first to third cells expressing the first and/or second enzyme(s) can be obtained by introducing the gene(s) encoding the first and/or second enzyme(s) to these host cell. The gene(s) to be introduced may be either the gene(s) encoding the first and/or second enzyme(s) or any of the first to third vectors carrying the gene(s) mentioned above. Examples of the methods for gene transfer include: a method of infecting a host cell with a vector; a physical method such as electroporation, particle gun (bombardment), and vacuum infiltration; and genome editing techniques such as CRISPR/Cas9.

The first to third cells thus obtained may transiently express the first and/or second enzyme(s) or may constantly express the enzyme(s). In the case of multicellular eukaryotic cells, these genes may be expressed either at all stages of development or only at a specific stage of development. These genes may also be expressed either in all tissues/organs or only in specific tissues/organs. Such control of the gene expression timing/site can be achieved, e.g., by appropriately selecting regulatory sequences.

The first to third cells according to the present invention may not be limited to cells in the first-generation modified to express the first and/or the second enzyme(s), but may also include cells in the subsequent generation(s) obtained by dividing such first-generation cells, as well as cells of progeny (including clones) obtained by sexual or asexual reproduction of individual(s) having such cells. When the first to third cells are plant cells, they may be cells of progeny (including clones) produced from a propagation material from the initial plant body (e.g., seeds, fruits, cuttings, tubers, tuberous roots, strains, callus, protoplasts, etc.).

EXAMPLES

Hereinafter, the present invention will be described in more detail with reference to examples. However, the present invention is not limited to the following examples and can be implemented in any form without departing from the spirit of the present invention.

In the following experiments, BL21(DE3) [Novagen, genotype F-, ompT, hsdSB (rB-mB-), gal (λcI857, ind1, Sam7, nin5, lacUV5-T7gene1), dcm (DE3)] was used as an *Escherichia coli* strain unless otherwise specified. The culture media used for culturing *Escherichia coli* were an LB medium (pH 7.0) having the following composition or a medium to which the components described below were added, which were sterilized using an autoclave at 121° C. for 15 minutes before use.

TABLE 1

| LB culture medium (pH 7.0) | |
|---|---|
| Trypsin | 10 g/L |
| Yeast extract | 5 g/L |
| Sodium chloride | 10 g/L |

The measurement conditions of high performance liquid chromatography (HPLC) and the evaluation conditions of enzyme activities by absorptiometry used in each of the following examples are described below.

[Measurement Conditions of High Performance Liquid Chromatography (HPLC)]

Apparatus: Hewlett Packerd 1200 infinity series

Column: Millipore-Merck Purospher STAR RP-18 end-capped column

Detection wavelength: 280 nm

Eluent A: 20 mM potassium phosphate (pH7.0)

Eluent B: 100% methanol

Program: 0 minutes (A:B=98%:2%)
7 minutes (A:B=98%:2%)
12 minutes (A:B=50%:50%)
17 minutes (A:B=50%:50%)
19 minutes (A:B=98%:2%)
23 minutes (A:B=98%:2%)

[Evaluation Conditions of Enzyme Activities by Absorptiometry]

Apparatus: BECKMAN COULTER DU800 UV/Vis Spectrophotometer
Amount of enzyme: 2 mg/mL
Buffer solution: 50 mM Tris-HCl buffer (pH=8.6)
Concentration of substrate: 0.3 mM to 9.6 mM
Volume: 200 μL
Measurement wavelength: From 4-nitrophenylalanine to 380 nm 4-nitrocinnamic acid: From phenylalanine to 305 nm cinnamic acid:
Measurement period: 10 minutes
Measurement temperature: 25° C.

Example 1

[I. Conversion of 4-Nitrophenylalanine to 4-Nitrocinnamic acid]

1. Construction of Plasmids and Their Introduction to *E. coli*

(1) Construction of pET28a-CamPAL and its Introduction to *E. coli*

CamPAL (an enzyme derived from *Camellia sinensis*) was artificially synthesized by a known polynucleotide synthesis method, and then subjected to restriction treatment with restriction enzymes NdeI and EcoRI. Plasmid pET28a (manufactured by Novagen) was also subjected to restriction treatment with restriction enzymes NdeI and EcoRI (hereinafter referred to as restriction-treated pET28a). The restriction-treated CamPAL was ligated to the restriction-treated pET28a using a DNA ligation kit Ligation High Ver.2 (manufactured by Toyobo Co., Ltd.) to prepare pET28a-CamPAL. The resultant pET28a-CamPAL was introduced to *E. coli* strain BL21(DE3) by the heat shock transformation method. The obtained CamPAL-producing *Escherichia coli* strain was cultured to express CamPAL.

(2) Construction of pET28a-LiePAL and its Introduction to *E. coli*

LiePAL (an enzyme derived from *Lithospermum erythrorhizon*) was artificially synthesized by a known polynucleotide synthesis method, and then subjected to restriction treatment using the same restriction enzymes as those used for the restriction treatment of CamPAL. The same procedure as that used for preparing pET28a-CamPAL was carried out except that the restriction-treated LiePAL was used instead of the restriction-treated CamPAL to prepare pET28a-LiePAL by the ligation to the restriction-treated pET28a. The resultant pET28a-LiePAL was introduced to *E. coli* strain BL21(DE3) in the same manner as mentioned above. The obtained LiePAL-producing *Escherichia coli* strain was cultured to express LiePAL.

(3) Construction of pET28a-RgPAL and its Introduction to *E. coli*

RgPAL (an enzyme derived from *Rhodotorula glutinis* JN-1) was artificially synthesized by a known polynucleotide synthesis method, and then subjected to restriction treatment using the same restriction enzymes as those used for the restriction treatment of CamPAL. The same procedure as that used for preparing pET28a-CamPAL was carried out except that the restriction-treated RgPAL was used instead of the restriction-treated CamPAL to prepare pET28a-RgPAL. The resultant pET28a-RgPAL was introduced to *E. coli* strain BL21(DE3) by the heat shock transformation method. The obtained RgPAL-producing *Escherichia coli* strain was cultured to express RgPAL.

2. Evaluation of the Enzyme Activities of Purified CamPAL, LiePAL, and RgPAL

Each of the CamPAL-, LiePAL-, and RgPAL-producing *Escherichia coli* strains was inoculated to 5 mL of LB medium containing 30 mg/L kanamycin sulfate, and cultured at 28° C. for 16 hours (hereinafter also may be referred to as "preculture"). The culture was inoculated to 200 mL of the same medium and cultured until the OD600 reached 0.6, after which isopropyl-β-thiogalactopyranoside (Isopropyl (β-D-1-thiogalactopyranoside: IPTG) was added at a final concentration of 0.5 mM, and the mixture was further cultured at 30° C. for 20 hours, with stirring at a rotation speed of 120 rpm. The cultured cells were collected, suspended in 20 mM Tris-HCl buffer (pH=7.5) containing 0.5 M NaCl, and ultrasonically disrupted. The suspension was centrifuged, the supernatant was purified using a His-Trap column, and the obtained enzyme was used for activity measurement.

The enzyme activity was measured and quantified by measuring the absorbance of the reaction product at the absorption wavelength for 10 minutes using an absorptiometer.

Specifically, regarding the deammonase activity for phenylalanine, 2 mg/mL of each of the above enzymes was added to 50 mM Tris-HCl buffer (pH=8.6) containing 0.3 to 9.6 mM phenylalanine to cause reaction, and the change in absorbance at a wavelength of 305 nm resulting from the formation of cinnamic acid was measured for 10 minutes. Regarding the deammonase activity for 4-nitrophenylalanine, 2 mg/mL of each of the above enzymes was added to 50 mM Tris-HCl buffer (pH=8.6) containing 0.3 to 9.6 mM 4-nitrophenylalanine to cause reaction, and the change in absorbance at a wavelength of 380 nm resulting from the formation of 4-nitrocinnamic acid was measured and quantified for 10 minutes.

FIG. 1 is a table showing the deammonase specific activities, $K_m$, $K_{cat}$, and $K_m/K_{cat}$ of CamPAL, LiePAL, and RgPAL purified after recombinant production in *Escherichia coli* on phenylalanine (Phe) and 4-nitrophenylalanine (n-Phe). It can be understood from these results that all of CamPAL, LiePAL, and RgPAL have a capacity to covert 4-nitrophenylalanine to 4-nitrocinnamic acid.

3. Evaluation of the Enzyme Activities of CamPAL, LiePAL, and RgPAL in Resting-Cell Reaction The CamPAL-, LiePAL-, and RgPAL-producing *Escherichia coli* strains mentioned above were precultured using 3 mL of LB medium containing 40 mg/L kanamycin sulfate at 28° C. for 16 hours with stirring at 300 rpm. 1 mL of this pre-cultured liquid was inoculated to 100 mL of LB medium containing 40 mg/L of kanamycin sulfate, cultured at 30° C. for 4 hours with shaking at 120 rpm, and after the addition of 0.5 mM of IPTG, incubated further for 20 hours. The obtained bacterial cells were washed twice with a reaction buffer (100 mM Tris-HCl buffer, pH 8.5).

The resting cells obtained were suspended in a reaction buffer and reacted at 28° C. with shaking at 300 rpm. 20 mM of 4-nitrophenylalanine was added to the medium every 24 hours while the reaction was continued. The reaction supernatant was periodically collected to quantify 4-nitrophenylalanine and 4-nitrocinnamic acid.

The supernatant was transferred to a centrifuge tube, collected by centrifugation, and the reaction product was quantified using high performance liquid chromatography (HPLC).

The same experiment was also performed using the host *Escherichia coli* as a control.

FIG. 2 is a graph showing the amount of 4-nitrocinnamic acid in the reaction supernatant 24 hours after the resting-cell reaction of the *Escherichia coli* strains producing CamPAL, LiePAL, and RgPAL. When any of the resting cells of the CamPAL-, LiePAL-, and RgPAL-producing *Escherichia coli* strains were used, the amount of 4-nitrocinnamic acid in the reaction supernatant was significantly higher than that of the control *Escherichia coli*. It can be understood from these results that the conversion of 4-nitrophenylalanine to 4-nitrocinnamic acid by CamPAL, LiePAL, and RgPAL proceeded.

Figure 3:
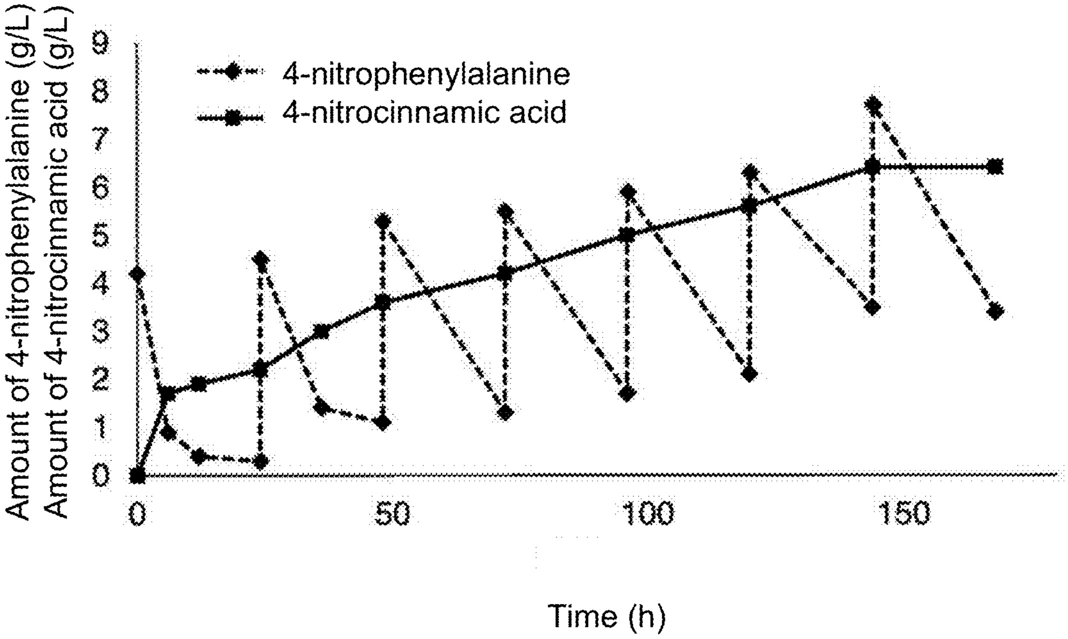
FIG. 3 is a graph showing the results of conversion reaction over time from 4-nitrophenylalanine to 4-nitrocinnamic acid by CamPAL, which was produced by genetically modified *E. coli* and then subjected to a resting cell.

FIG. 3 is a graph showing the time-dependent changes in the amounts of 4-nitrophenylalanine and 4-nitrocinnamic acid in the reaction supernatant of the resting-cell reaction of the CamPAL-producing *Escherichia coli* strain. The amount of 4-nitrophenylalanine in the reaction supernatant increased due to its addition every 24 hours, but then gradually decreased until the next addition, while the amount of 4-nitrocinnamic acid in the reaction supernatant continued to increase. It can be understood from these results that the conversion of 4-nitrophenylalanine to 4-nitrocinnamic acid by CamPAL proceeded continuously.

[II. Conversion of 4-Nitrocinnamic Acid to 4-Aminocinnamic Acid]

1. Construction of Plasmids and their Introduction to *E. coli*

(1) Construction of pRSFDuet-1-scFrm2 and its introduction to *E. coli*

The gene of scFrm2S, an enzyme derived from *Saccharomyces cerevisiae* (its amino acid sequence is shown in SEQ ID NO: 7 and an example of its nucleotide sequence is shown in SEQ ID NO: 8) was amplified from a *Saccharomyces cerevisiae* genomic library by PCR using primers 5'-AACGGATCCGATGTCCCCAACTGGAAAC-3' (SEQ ID NO: 17) and 5'-GCCAAGCTTCAGTGATAAACGTTGATTACG-3' (SEQ ID NO: 18). The amplified gene was then subjected to restriction treatment with restriction enzymes BamHI and HindIII, while plasmid pRSFDuet-1 (Novagen) was also subjected to restriction treatment with the same restriction enzymes BamHI and HindIII. The restriction-treated scFrm2S was ligated to the restriction-treated pRSFDuet-1 using a DNA ligation kit Ligation High Ver.2 (manufactured by Toyobo Co., Ltd.) to prepare pRSFDuet-1-scFrm2. The resultant pRSFDuet-1-scFrm2 was introduced to *E. coli* strain BL21(DE3) by the heat shock transformation. The obtained scFrm2-producing *Escherichia coli* strain was cultured to express scFrm2.

(2) Construction of pRSFDuet-1-scHbn1 and its Introduction to *E. coli*

The gene of scHbn1, an enzyme derived from *Saccharomyces cerevisiae* (its amino acid sequence is shown in SEQ ID NO: 9 and an example of its nucleotide sequence is shown in SEQ ID NO: 10) was amplified from a *Saccharomyces cerevisiae* genomic library by PCR using primers 5'-AACGGATCCGATGTCTGCTGTTGCAAC-3' (SEQ ID NO:19) and 5'-GCCAAGCTTAATTGAAGATTTCAACATCG-3' (SEQ ID NO:20). The amplified gene was subjected to restriction treatment in the same manner as the restriction treatment of the ScFrm2, and then ligated to the plasmid to prepare pRSFDuet-1-scHbn1. The resulting pRSFDuet-1-scHbn1 was introduced to *E. coli* strain BL21 (DE3) by the heat shock transformation. The obtained scHbn1-producing *Escherichia coli* strain was cultured to express scHbn1.

(3) Construction of pRSFDuet-1-cdFLDZ and its Introduction to *E. coli*

The gene of cdFLDZ, an enzyme derived from *Clostridium difficile* (its amino acid sequence is shown in SEQ ID NO: 11 and an example of its nucleotide sequence is shown in SEQ ID NO: 12) was amplified from a *Saccharomyces cerevisiae* genomic library by PCR using primers 5'-CCGGGATCCAATGAAGATTAGTTCTATG-3' (SEQ ID NO:21) and 5'-CCGGAATTCTTATATATTTAATGCTAC-33' (SEQ ID NO:22). The amplified gene was subjected to restriction treatment in the same manner as the restriction treatment of the ScFrm2, and then ligated to the plasmid to prepare pRSFDuet-1-cdFLDZ. The resulting pRSFDuet-1-cdFLDZ was introduced to *E. coli* strain BL21 (DE3) by the heat shock transformation. The obtained cdFLDZ-producing *Escherichia coli* strain was cultured to express cdFLDZ.

2. Evaluation of the Enzyme Activities by scFrm2, scHbn1, and cdFLDZ in Resting-Cell Reactions Each of the scFrm2-, scHbn1-, and cdFLDZ-producing *Escherichia coli* strains were precultured using 3 mL of LB medium containing 30 mg/L kanamycin sulfate at 28° C. for 16 hours with shaking at 300 rpm. 1 mL of this preculture liquid was inoculated to 100 mL of LB medium containing 30 mg/L kanamycin sulfate, cultured at 30° C. for 4 hours with shaking at 120 rpm, and after 0.1 mM IPTG was added, incubated further at 20° C. for 12 hours. The obtained bacterial cells were washed twice with a reaction buffer (100 mM potassium dihydrogen phosphate ($KH_2PO_4$), 1 mM magnesium sulfate ($MgSO_4$), 0.5 mM thiamine chloride, pH 7.0).

The resting cells thus obtained were suspended in a reaction buffer containing 2.5 mM 4-nitrocinnamic acid, and reacted at 30° C. for 12 hours with shaking at 300 rpm. After the reaction, the reaction supernatant was collected to quantify 4-aminocinnamic acid. The supernatant was transferred to a centrifuge tube, collected by centrifugation, and the reaction product was quantified using the above HPLC.

The same experiment was also performed using the host *Escherichia coli* as a control.

Figure 4:
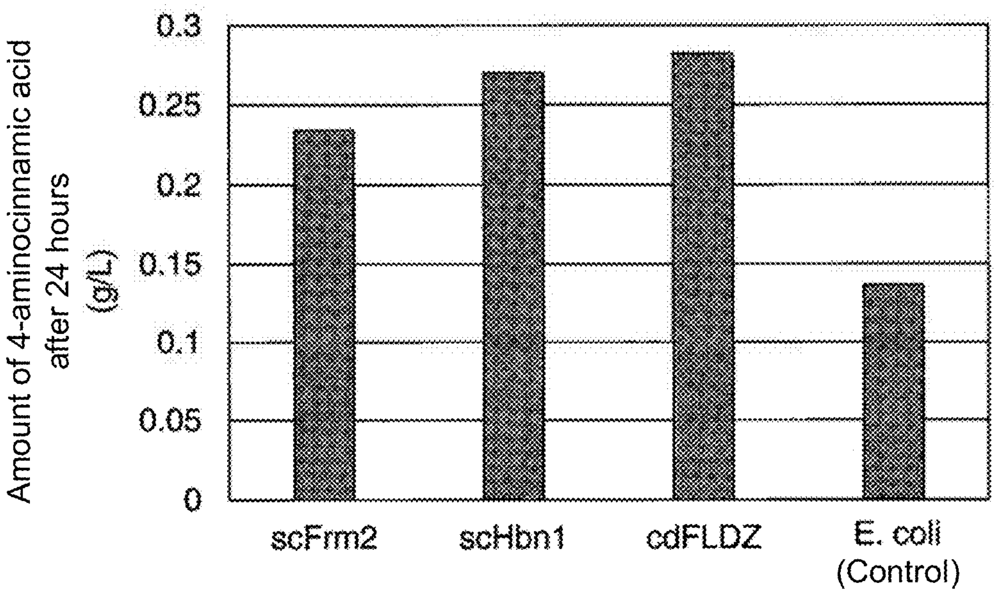
FIG. 4 is a graph showing the activities of scFrm2, scHbn1, and cdFLDZ, which were produced by genetically modified *E. coli* and then subjected to a resting-cell reaction, to convert 4-nitrocinnamic acid to 4-aminocinnamic acid.

FIG. 4 is a graph showing the activities of scFrm2, scHbn1, and cdFLDZ produced by recombinant *Escherichia coli* and then subjected to a resting-cell reaction in converting 4-nitrocinnamic acid to 4-aminocinnamic acid. In any of the resting cells of the scFrm2-, scHbn1-, and cdFLDZ-producing *E. coli* strains, the amount of 4-aminocinnamic acid in the medium supernatant was remarkably increased as compared with the control *E. coli*, It can be understood from these results that the conversion of 4-nitrocinnamic acid to 4-aminocinnamic acid by scFrm2-, scHbn1-, and cdFLDZ proceeded. In addition, the control *Escherichia coli* produced 4-aminocinnamic acid. It was proved from these results that *Escherichia coli* has the capacity to cause the reduction reaction of 4-nitrocinnamic acid to 4-aminocinnamic acid.

Example 2

[III. Conversion of 4-Nitrophenylalanine to 4-Nitrocinnamic acid]

1. Evaluation of Conversion Efficiencies by CamPAL in Different Bacteria Mass and/or Substrate Mass The CamPAL-producing *Escherichia coli* strain described in Example 1 was pre-cultured using 5 mL of LB medium containing 40 mg/L kanamycin sulfate at 28° C. for 16 hours with stirring at 300 rpm. 1 mL of this pre-cultured solution was inoculated to 100 mL of TB medium having the following composition after the addition of 80 mg/L kanamycin sulfate, and cultured at 30° C. for 4 hours with shaking at 120 rpm. After the addition of 0.1 mM of IPTG, the cells were further cultured for 20 hours, recovered from the culture solution by centrifugation, and stored at −80° C. The frozen cells thus obtained were weighed at 10 g/L, 20 g/L and 30 g/L, while the substrate 4-nitrophenylalanine was also weighed at 4.2 g/L, 21 g/L, and 42 g/L.

TABLE 2

| TB culture medium (pH 7.0) | |
|---|---|
| Tryptone | 12 g/L |
| Yeast extract | 24 g/L |
| $KH_2PO_4$ | 2.31 g/L |
| $K_2HPO_4$ | 12.54 g/L |
| Glycerol | 8 mL |

Each mass of the cells and each mass of the substrate were suspended in a reaction buffer (100 mM Tris-HCl buffer, pH 8.5), and a resting microbial cell reaction was carried out at 37° C. with stirring at 300 rpm. After the reaction for 24 hours, the reaction solution was collected, and the amounts of 4-nitrophenylalanine and 4-nitrocinnamic acid were quantified. For the quantification of each reaction product, the supernatant of the obtained (bacterial cell) reaction solution was transferred to a centrifuge tube, collected by centrifugation, and the reaction product was quantified using the HPLC mentioned above.

FIG. 5 shows the results of suspending each cell mass and each substrate mass in the reaction buffer and causing a reaction for 24 hours. It can be understood from these results that when the cell mass was 20 g/L or 30 g/L and the substrate mass was 21 g/L, the conversion efficiency of 4-nitrophenylalanine to 4-nitrocinnamic acid was as high as the yield of 60% or more.

2. Conversion Reaction of 4-Nitrophenylalanine to 4-Nitrocinnamic Acid

The CamPAL-producing *Escherichia coli* strain described in Example 1 was used (cell mass: 20 g/L to 30 g/L) was used in a reaction of converting the substrate 4-nitrophenylalanine (group weight 21 g/L) to 4-nitrocinnamic acid, using a 2 L jar fermenter (BNR-C-2LS manufactured by Maruhishi Bio Engineering Co., Ltd.) as a reactor.

Specifically, the CamPAL-producing *Escherichia coli* strain was precultured using 15 mL of LB medium with 40 mL/L kanamycin sulfate at 28° C. for 16 hours with stirring at 300 rpm. 12 mL of this preculture liquid was inoculated to a 2 L jar fermenter containing 1.2 L TB medium with 80 mg/L kanamycin sulfate, and cultured at 30° C. for 4 hours with aeration of 3.5 L/min and stirring at 500 rpm. Subsequently, 0.1 mM IPTG was added to this culture solution, and the culture was continued for another 20 hours. The mass of bacterial cells calculated from the value of OD600 was 30 g/L.

After completion of the culture, 21 g/L of 4-nitrophenylalanine was added to the culture medium as the substrate, and the pH was adjusted to 8.5 using a 2N NaOH aqueous solution. This culture solution was stirred at 500 rpm and allowed to react at 37° C. for 24 hours without aeration. The reaction solution was collected during the reaction, and 4-nitrophenylalanine and 4-nitrocinnamic acid were quantified as follows: the reaction solution was transferred to a centrifuge tube, the supernatant was recovered by centrifugation, and the reaction product was quantified using HPLC under the above conditions.

Figure 6:
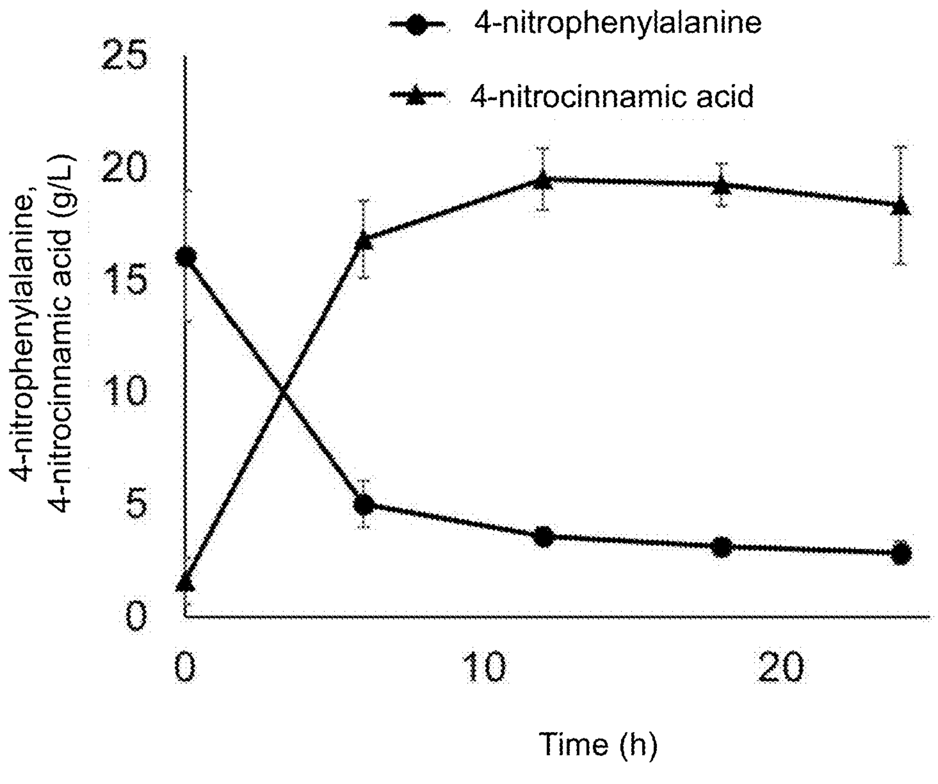
FIG. 6 is a graph indicating the results of conversion reaction over time from 4-nitrophenylalanine to 4-nitrocinnamic acid by CamPAL, which was produced by *E. coli* cultured in a 1.2 L scale and then subjected to a conversion reaction in a reaction vessel.

FIG. 6 is a graph showing the analysis results of the reaction solution after the reaction for 24 hours. It can be understood from these results that high conversion efficiency was achieved, with 21 g/L of 4-nitrophenylalanine converted to 18 g/L of 4-nitrocinnamic acid. When the same reaction was also carried out for 24 hours, with changing the aeration rate to 0.04 L/min, high conversion efficiency was achieved again, with 21 g/L of 4-nitrophenylalanine converted to 12 g/L of 4-nitrocinnamic acid.

Purification of 4-nitrocinnamic acid was carried out from a 1.2 L reaction solution of the CamPAL-producing *Escherichia coli*. After the reaction for 24 hours, the bacterial cells were removed by centrifugation, and 12N HCl was added to the reaction solution supernatant to adjust the pH to 5 to cause precipitation. The precipitate was collected by filtration, washed with acetone, and dried. The solid product recovered after drying was subjected to HPLC analysis under the above conditions.

Figure 7:
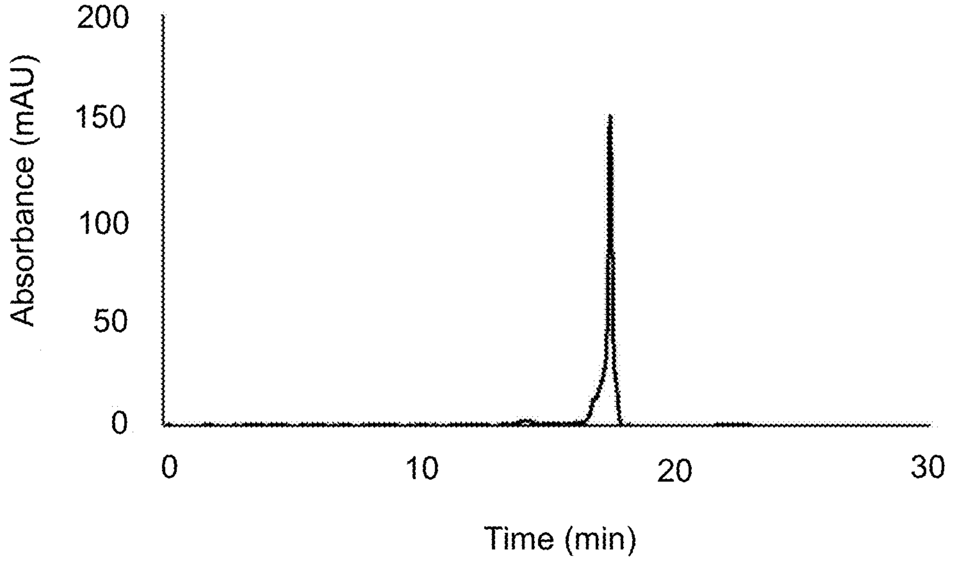
FIG. 7 is a graph showing the results of HPLC analysis of purified 4-nitrocinnamic acid.

FIG. 7 is a graph showing the HPLC analysis results of the obtained product. The results showed that the product was 4-nitrocinnamic acid, and the conversion reaction of 4-nitrophenylalanine to 4-nitrocinnamic acid occurred. It can also be understood from these results that 4-nitrocinnamic acid was obtained with a purity of 97% and a yield of 93%, which purity and yield were extremely high. The purity of the obtained 4-nitrocinnamic acid is sufficient to be converted to 4-aminocinnamic acid by a chemical reduction method.

Example 3

[IV. Conversion Reaction of 4-Nitrophenylalanine to 4-Aminocinnamic Acid]

1. Search for Suitable Carbon Source for Conversion of 4-Nitrocinnamic Acid to 4-Aminocinnamic Acid

*E. coli* is known to have nitroreductase (nfsA and nfsB). A reduction reaction of 4-nitrocinnamic acid to 4-aminocinnamic acid was carried out using *Escherichia coli.*

The CamPAL-producing *Escherichia coli* strain described in Example 1 was first precultured for 16 hours in the same manner as in Example 2. 1 mL of this pre-cultured liquid was inoculated to 100 mL of TB medium containing 80 mg/L kanamycin sulfate, cultured at 30° C. for 4 hours with stirring at 120 rpm, and after the addition of 0.1 mM IPTG, cultured further for 16 hours. 2 g/L of 4-nitrocinnamic acid was added to the resultant culture solution, the pH was adjusted to 8 using 2N NaOH, and glucose, fructose, or glycerol was added as a carbon source at a final concentration of 10%. The cells were cultured at 37° C. for 24 hours with stirring at 300 rpm to cause reaction.

During the reaction, the reaction solution was collected, and 4-aminocinnamic acid was quantified. Specifically, the reaction solution was transferred to a centrifuge tube, the supernatant was recovered by centrifugation, and the reaction product was quantified using the HPLC.

Figure 8:
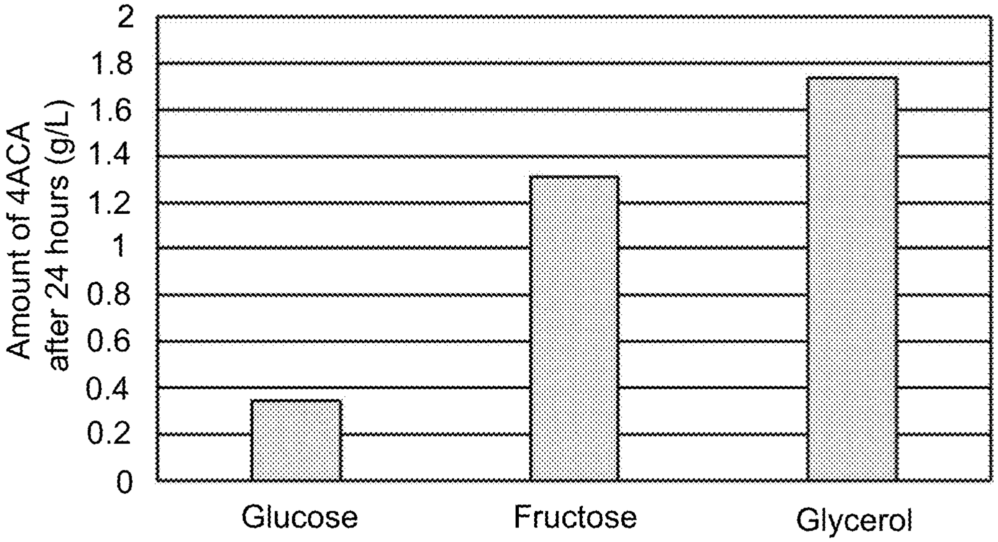
FIG. 8 is a graph showing the results of conversion from 4-nitrocinnamic acid to 4-aminocinnamic acid (4ACA) by adding glucose, fructose and glycerol to a culture solution of CamPAL-producing *E. coli;*

FIG. 8 is a graph showing the conversion reaction of 4-nitrocinnamic acid to 4-aminocinnamic acid when glucose, fructose, or glycerol was added to the culture medium of the CamPAL-producing *Escherichia coli* strain at a final concentration of 10%. It can be understood from these results that the largest amount of 4-aminocinnamic acid was obtained when glycerol was added. It can thus be understood that glycerol is suitable as a carbon source to be added in the conversion reaction of 4-nitrocinnamic acid to 4-aminocinnamic acid.

2. Conversion of 4-Nitrophenylalanine to 4-Aminocinnamic Acid

Conversion of 4-nitrophenylalanine to 4-aminocinnamic acid was carried out using a 1 L jar fermenter (manufactured by Biott: BMJ-01), in the presence of glycerol under the conditions mentioned above. Specifically, 5 mL of the preculture liquid of Example 2 was inoculated to a 1 L jar fermenter containing 0.5 L of TB medium supplemented with 80 mg/L kanamycin sulfate, and cultured at 30° C. for 4 hours, with aeration at 0.7 L/min and stirring at 645 rpm. 0.1 mM IPTG was then added, and the culturing was continued for another 20 hours.

After the completion of the culturing, 7 g/L of 4-nitrophenylalanine and glycerol at a final concentration of 10% were added to the culture solution, and the pH was adjusted to 8.5 with 2N NaOH. The reaction was carried out at 37° C. for 36 hours with an air flow rate of 0.02 L/min and stirring at 645 rpm. When the pH dropped below 8.0, 2N NaOH was added. During the reaction, the reaction solution was sampled, and 4-nitrophenylalanine, 4-nitrocinnamic acid and 4-aminocinnamic acid were quantified.

Figure 9:
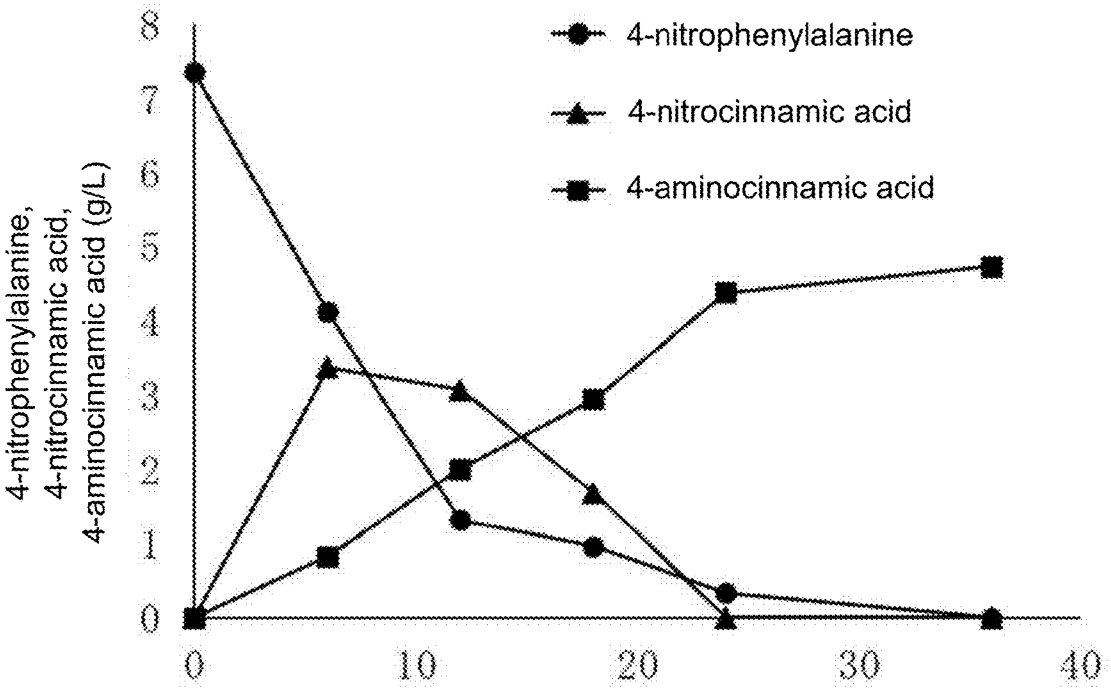
FIG. 9 is a graph showing the conversion activity of CamPAL-producing *E. coli* from 4-nitrophenylalanine to 4-aminocinnamic acid.

FIG. 9 is a graph showing the capacity of the CamPAL-producing *Escherichia coli strain to convert* 4-nitrophenylalanine to 4-aminocinnamic acid. It can be understood from these results that 4.7 g/L of 4-aminocinnamic acid was produced from 7 g/L of 4-nitrophenylalanine as a raw material.

Purification of 4-aminocinnamic acid was carried out from 0.5 L of the reaction solution. Specifically, after the reaction for 24 hours, the cells were removed from the reaction solution by centrifugation, and 12N HCl was added to the resulting supernatant to adjust the pH to 3. 600 mL of the reaction solution supernatant was mixed with 700 g of a strongly acidic cation exchange resin (Mitsubishi Chemical Corporation) (Manufactured by: Diaion PK212LH) and stirred for 1 hour. The resin was collected, washed with distilled water in an amount of double the amount of the resin, and further washed with ethanol in an amount of twice the amount of the resin. 7.5% aqueous ammonia in an amount of 1.5 times the amount of the resin was added to elute 4-aminocinnamic acid. 7.5% aqueous ammonia in an amount of 0.5 times the amount of the resin was added to rinse the resin, and an eluate containing 4-aminocinnamic acid was obtained. The eluate was concentrated with an evaporator, and then adjusted to pH 3 with 12N HCl. Then, an equal amount of ethyl acetate was added, the mixture was stirred for 1 hour, and the ethyl acetate layer was collected by centrifugation. Ethyl acetate was removed using an evaporator, and a crude product of 4-aminocinnamic acid was recovered.

A crude product of 4-aminocinnamic acid was dissolved in acetone, insoluble substances were removed by filtration, and 12N HCl was added to precipitate the hydrochloride salt of 4-aminocinnamic acid. The precipitate was collected by filtration, washed with acetone, and dried to obtain a solid dried product. The solid product recovered after drying was subjected to HPLC analysis under the above conditions.

Figure 10:
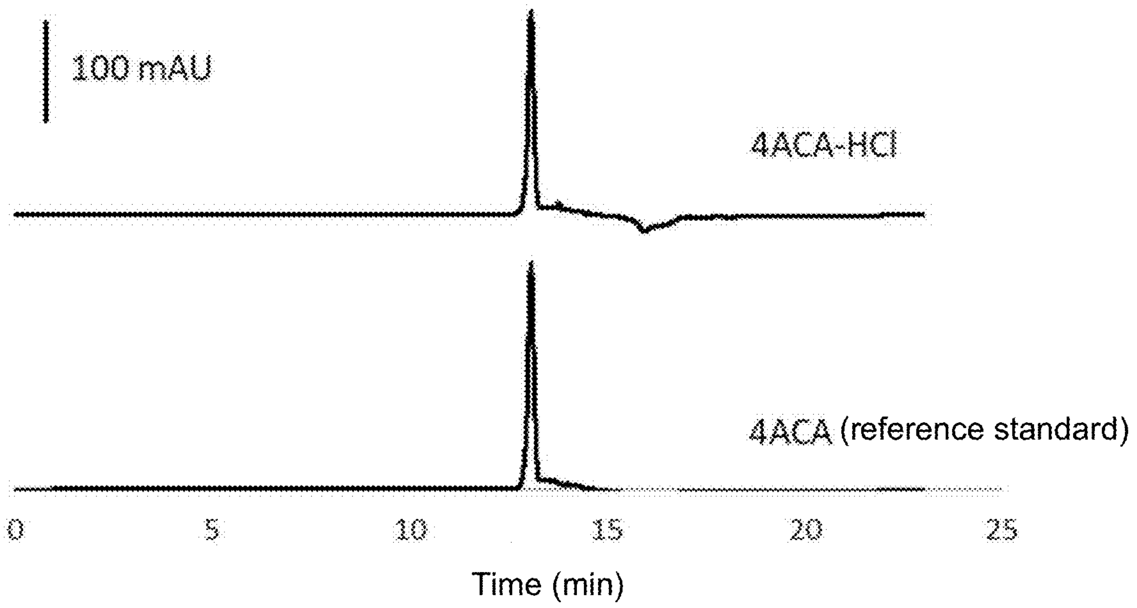
FIG. 10 is a graph showing the results of HPLC analysis of purified 4ACA hydrochloride and 4ACA (reference standard).

FIG. 10 is a graph showing the results of HPLC analysis of the obtained product and 4-aminocinnamic acid (reference standard). These results show that the product was 4-aminocinnamic acid, indicating that a conversion reaction of 4-nitrophenylalanine to 4-aminocinnamic acid using nitroreductase (reduction reaction) of *Escherichia coli* actually occurred. The obtained 4-aminocinnamic acid had an extremely high purity of 98%. The recovery rate of 4-aminocinnamic acid was 60%.

Example 4

[Conversion of 4-Nitrocinnamic Acid to 4-Aminocinnamic Acid]

1. Construction of Plasmids and their Introduction to *E. coli*

(1) Construction of pCDF Duet-1-nfsA and its Introduction to *E. coli*

The gene of *Escherichia coli*-derived enzyme nfsA (its amino acid sequence is shown in SEQ ID NO: 13 and an example of its nucleotide sequence is shown in SEQ ID NO: 14) was amplified from a genomic library of *Escherichia coli* by PCR, using primers 5'-CAGACCATGGGCACGCCAACCATTGAACTTTATTTGTG -3' (SEQ ID NO: 23) and 5'-GAGGATCCCTTAGCGCGCTCGCCCAACCCTG-3' (SEQ ID NO: 24). The amplified gene was then subjected to restriction treatment with restriction enzymes NcoI and BamHI, while plasmid pCDF Duet-1 (Novagen) was similarly subjected to restriction treatment with the restriction enzymes NcoI and BamHI. The restriction-treated amplified gene was ligated to the restriction-treated pCDF Duet-1 with a DNA ligation kit Ligation High Ver.2 (manufactured by Toyobo Co., Ltd.) to prepare pCDF Duet-1-nfsA. The obtained pCDF Duet-1-nfsA was introduced to *E. coli* strain BL21(DE3) by heat shock transformation. The obtained nfsA-producing *Escherichia coli* strain was cultured to express nfsA.

(2) Construction of pCDF Duet-1-nfsB and its Introduction to *E. coli*

The gene of *Escherichia coli*-derived enzyme nfsB (its amino acid sequence is shown in SEQ ID NO: 15 and an example of its nucleotide sequence is shown in SEQ ID NO: 16) was amplified from a genomic library of *Escherichia coli* by PCR, using primers 5'-CAGACCATGGGCGATATCATTTCTGTCGCC-3' (SEQ ID NO:25) and 5'-GAGGATCCTTACACTTCGGTTAAGGTGATG-3' (SEQ ID NO:26). The amplified gene was then subjected to restriction treatment in the same manner as the restriction treatment of the nfsA and ligated to the plasmid to prepare pCDF Duet-1-nfsA. The obtained pCDF Duet-1-nfsB was introduced to *E. coli* strain BL21(DE3) by heat shock transformation. The obtained nfsB-producing *Escherichia coli* strain was cultured to express nfsB.

2. Evaluation of the Enzyme Activities by nfsA and nfsB in Resting-Cell Reactions Each of the nfsA- and nfsB-producing *Escherichia coli* strains was precultured using 5 mL of LB medium containing 40 mg/L of streptomycin sulfate at 28° C. for 16 hours with shaking at 300 rpm. 1 mL of this pre-cultured solution was inoculated to 100 mL of TB medium containing 80 mg/L streptomycin sulfate, cultured at 30° C. for 4 hours with shaking at 120 rpm. 0.1 mM IPTG was added, and the culture was further incubated at 30° C. for another 18 hours.

The pH of the culture medium containing the obtained bacterial cells was adjusted to 8.0 by addition of 2N NaOH. 2 g/L of 4-nitrocinnamic acid and 2% final concentration of glycerol were suspended in this culture medium, and the reaction was carried out at 37° C. for 18 hours with shaking at 120 rpm. After the reaction, the reaction solution supernatant was collected to quantify 4-aminocinnamic acid. Specifically, the supernatant was transferred to a centrifuge tube, collected by centrifugation, and the reaction product was quantified using the above HPLC.

The same experiment was also carried out using the host *Escherichia coli* as a control.

These results show that the nfsA-producing *Escherichia coli* strain achieved conversion to 0.26 g/L of 4-aminocinnamic acid, the nfsB-producing *Escherichia coli* strain to 0.76 g/L of 4-aminocinnamic acid, and the control *Escherichia coli* strain to 32 g/L 4-aminocinnamic acid. It can be understood from these results that the conversion of 4-nitrocinnamic acid to 4-aminocinnamic acid by nfsA and nfsB actually proceeded.

INDUSTRIAL APPLICABILITY

The present invention can be widely used in fields requiring synthesis of 4-aminocinnamic acid from glucose such as biomass, and therefore has high industrial utility.

The invention claimed is:

1. A method for producing 4-aminocinnamic acid from 4-nitrophenylalanine, comprising the steps of:

(1) converting 4-nitrophenylalanine to 4-nitrocinnamic acid by using a first enzyme which consists of an amino acid sequence having a sequence identity of 90% or more to the amino acid sequence defined in SEQ ID NOs:1, 3, or 5 and which has the ability to convert 4-nitrophenylalanine to 4-nitrocinnamic acid; and (2) converting 4-nitrocinnamic acid to 4-aminocinnamic acid by using a second enzyme which consists of an amino acid sequence having a sequence identity of 90% or more to the amino acid sequence defined in SEQ ID NOs:7, 9, 11, 13, or 15 and which has the ability to convert 4-nitrocinnamic acid to 4-aminocinnamic acid.

2. The method according to claim 1, wherein the conversion of step (1) is carried out with a first host cell which has been engineered to express the first enzyme.

3. The method according to claim 2, wherein the first host cell is a microorganism cell.

4. The method according to claim 3, wherein the microorganism is a bacterium.

5. The method according to claim 4, wherein the conversion of step (1) is carried out via a resting-cell reaction using a resting bacterial cell as the first host cell.

6. The method according to claim 1, wherein the conversion of step (2) is carried out by using a second host cell which expresses the second enzyme.

7. The method according to claim 6, wherein the second host cell is a host cell engineered to express the second enzyme.

8. The method according to claim 6, wherein the second host cell is a microorganism cell.

9. The method according to claim 8, wherein the microorganism is a bacterium.

10. The method according to claim 9, wherein the conversion of step (2) is carried out via a resting-cell reaction using a resting bacterial cell as the second host cell.

11. The method according to claim 5, wherein the resting bacterial cell is selected from the group consisting of cultured cells, powdered cells, and immobilized cells.

12. The method according to claim 1, wherein the conversion of step (2) is carried out at a pH of from 8 to 9.

13. A method for producing 4-aminocinnamic acid from glucose, comprising the steps of:

(a) producing phenylalanine from glucose;

(b) converting the phenylalanine obtained in step (a) to 4-nitrophenylalanine via nitration; and (c) producing 4-aminocinnamic acid from the 4-nitrophenylalanine obtained in step (b) via a method according to claim 1.

14. A method for producing 4-aminocinnamic acid from phenylalanine, comprising the steps of:

(b) converting phenylalanine to 4-nitrophenylalanine via nitration; and (c) producing 4-aminocinnamic acid from the 4-nitrophenylalanine obtained in step (b) via a method according to claim 1.

15. A method for producing 4-nitrocinnamic acid from 4-nitrophenylalanine, comprising:

using a first enzyme which consists of an amino acid sequence having a sequence identity of 90% or more to the amino acid sequence defined in SEQ ID NOs:1, 3, or 5 and which has the ability to convert 4-nitrophenylalanine to 4-nitrocinnamic acid.

16. A method for producing 4-aminocinnamic acid from 4-nitrocinnamic acid, comprising:

using a second enzyme which consists of an amino acid sequence having a sequence identity of 90% or more to the amino acid sequence defined in SEQ ID NOs:7, 9, 11, 13, or 15 and which has the ability to convert 4-nitrocinnamic acid to 4-aminocinnamic acid.

17. The method according to claim 10, wherein the resting bacterial cell is selected from the group consisting of cultured cells, powdered cells, and immobilized cells.

* * * * *

SEQUENCE LISTING

```
<160> NUMBER OF SEQ ID NOS: 26

<210> SEQ ID NO 1
<211> LENGTH: 714
<212> TYPE: PRT
<213> ORGANISM: Camellia sinensis
<220> FEATURE:
<223> OTHER INFORMATION: CamPAL Polypeptide

<400> SEQUENCE: 1

Met Asp Ser Thr Thr Ala Ile Gly Asn Gly Val Gly Ser Gly Gly Ser
1               5                   10                  15

Pro Gly Phe Cys Leu Lys Asp Pro Leu Asn Trp Gly Val Ala Ala Glu
            20                  25                  30

Ala Met Lys Gly Ser His Leu Glu Glu Val Lys Gly Met Val Glu Glu
        35                  40                  45

Phe Arg Lys Pro Val Val Arg Leu Gly Gly Glu Thr Leu Thr Ile Ser
    50                  55                  60

Gln Val Ala Ala Ile Ala Val Arg Gly Ser Glu Val Ala Val Glu Leu
65                  70                  75                  80

Ser Glu Ser Ala Arg Glu Gly Val Lys Ala Ser Ser Asp Trp Val Met
                85                  90                  95

Glu Ser Met Asn Lys Gly Thr Asp Ser Tyr Gly Val Thr Thr Gly Phe
            100                 105                 110

Gly Ala Thr Ser His Arg Arg Thr Lys Glu Gly Gly Ala Leu Gln Lys
        115                 120                 125

Glu Leu Ile Arg Phe Leu Asn Ala Gly Ile Phe Gly Asn Gly Thr Glu
    130                 135                 140

Ser Cys His Thr Leu Pro Gln Ser Ala Thr Arg Ala Ala Met Leu Val
145                 150                 155                 160

Arg Ile Asn Thr Leu Leu Gln Gly Tyr Ser Gly Ile Arg Phe Glu Ile
                165                 170                 175

Leu Glu Ala Ile Ser Lys Phe Leu Asn Asn Asn Ile Thr Pro Cys Leu
            180                 185                 190

Pro Leu Arg Gly Thr Ile Thr Ala Ser Gly Asp Leu Val Pro Leu Ser
        195                 200                 205

Tyr Ile Ala Gly Leu Leu Thr Gly Arg His Asn Ser Lys Ala Val Gly
    210                 215                 220

Pro Thr Gly Glu Ile Leu His Pro Lys Glu Ala Phe Arg Leu Ala Gly
225                 230                 235                 240

Val Glu Gly Gly Phe Phe Glu Leu Gln Pro Lys Glu Gly Leu Ala Leu
                245                 250                 255

Val Asn Gly Thr Ala Val Gly Ser Gly Leu Ala Ser Met Val Leu Phe
            260                 265                 270

Glu Ala Asn Ile Leu Ala Val Leu Ser Glu Val Leu Ser Ala Ile Phe
        275                 280                 285

Ala Glu Val Met Gln Gly Lys Pro Glu Phe Thr Asp His Leu Thr His
    290                 295                 300

Lys Leu Lys His His Pro Gly Gln Ile Glu Ala Ala Ala Ile Met Glu
305                 310                 315                 320
```

-continued

```
His Ile Leu Asp Gly Ser Ser Tyr Val Lys Ala Ala Gln Lys Leu His
                325                 330                 335

Glu Met Asp Pro Leu Gln Lys Pro Lys Gln Asp Arg Tyr Ala Leu Arg
            340                 345                 350

Thr Ser Pro Gln Trp Leu Gly Pro Leu Ile Glu Val Ile Arg Ser Ser
        355                 360                 365

Thr Lys Ser Ile Glu Arg Glu Ile Asn Ser Val Asn Asp Asn Pro Leu
    370                 375                 380

Ile Asn Val Ser Arg Asn Lys Ala Leu His Gly Gly Asn Phe Gln Gly
385                 390                 395                 400

Thr Pro Ile Gly Val Ser Met Asp Asn Thr Arg Leu Ala Val Ala Ser
                405                 410                 415

Ile Gly Lys Leu Met Phe Ala Gln Phe Ser Glu Leu Val Asn Asp Phe
            420                 425                 430

Tyr Asn Asn Gly Leu Pro Ser Asn Leu Ser Gly Gly Arg Asn Pro Ser
        435                 440                 445

Leu Asp Tyr Gly Phe Lys Gly Ala Glu Ile Ala Met Ala Ala Tyr Cys
    450                 455                 460

Ser Glu Leu Gln Phe Leu Ala Asn Pro Val Thr Asn His Val Gln Ser
465                 470                 475                 480

Ala Glu Gln His Asn Gln Asp Val Asn Ser Leu Gly Leu Ile Ser Ser
                485                 490                 495

Arg Lys Thr Ala Glu Ala Val Asp Ile Leu Lys Leu Met Ser Ser Thr
            500                 505                 510

Tyr Leu Val Ala Leu Cys Gln Ala Val Asp Leu Arg His Phe Glu Glu
        515                 520                 525

Asn Leu Arg Asn Thr Val Lys Ser Thr Val Ser Gln Val Ala Lys Arg
    530                 535                 540

Val Leu Thr Met Gly Val Asn Gly Glu Leu His Pro Ser Arg Phe Cys
545                 550                 555                 560

Glu Lys Asp Leu Leu Arg Val Val Asp Arg Glu Tyr Ile Phe Ala Tyr
                565                 570                 575

Ile Asp Asp Pro Cys Ser Ala Thr Tyr Pro Leu Met Gln Lys Leu Arg
            580                 585                 590

Gln Val Leu Val Glu His Ala Leu Lys Asn Gly Glu Ser Glu Lys Asn
        595                 600                 605

Leu Ser Thr Ser Ile Phe Gln Lys Ile Arg Ala Phe Glu Glu Glu Ile
    610                 615                 620

Lys Thr Leu Leu Pro Lys Glu Val Glu Ser Thr Arg Ala Ala Ile Glu
625                 630                 635                 640

Asn Gly Asn Ser Ala Ile Pro Asn Arg Ile Lys Glu Cys Arg Ser Tyr
                645                 650                 655

Pro Leu Tyr Lys Phe Val Arg Glu Glu Leu Gly Thr Glu Leu Leu Thr
            660                 665                 670

Gly Glu Lys Val Arg Ser Pro Gly Glu Glu Phe Asp Lys Val Phe Thr
        675                 680                 685

Ala Leu Cys Lys Gly Glu Met Ile Asp Pro Leu Met Asp Cys Leu Lys
    690                 695                 700

Glu Trp Asn Gly Ala Pro Leu Pro Ile Cys
705                 710
```

<210> SEQ ID NO 2
<211> LENGTH: 2118
<212> TYPE: DNA

-continued

<213> ORGANISM: Camellia sinensis
<220> FEATURE:
<223> OTHER INFORMATION: CamPAL DNA

<400> SEQUENCE: 2

```
atggaaaacg gcaacggtaa aatggaattt tgcatgaaag atccgctgaa ttggggcatg     60
gcggccgaat ccatgaaagg ttcacatctg gacgaagtga agaaaatggt tgcggaattt    120
cgtaaaccgg tggttcagct ggccggcaaa accctgacga tcgcacaagt tgcagctatt    180
gcggcccgtg atgacggcgt taccgtcgaa ctggccgaag cagctcgcga aggtgtcaaa    240
gcaagctctg attgggtgat ggaatccatg aataaaggca ccgacagcta tggcgtgacc    300
acgggctttg gtgctacctc tcaccgtcgc acgaaacagg gcggtgcgct gcaaaaagaa    360
ctgatccgct ttctgaacgc cggtattttc ggcaatggta ccgaaacgtc gcataccctg    420
ccgcacagcg caacccgtgc cgcaatgctg gtgcgcatta acaccctgct gcagggctat    480
agcggtattc gttttgaaat cctggaagca attacgaaat tcctgaacac caatattacg    540
ccgtgtctgc cgctgcgtgg taccattacc gcaagcggtg atctggttcc gctgagctac    600
atcgctggcc tgctgaccgg tcgtccgaat agcaaagccg tcggcccgac gggtgaaaaa    660
ctgaacgccg aagaagcatt tcgcctggcc ggcattagtt ccggcttttt cgaactgcag    720
ccgaaagaag gcctggcact ggttaatggt accgctgtcg gctcgggtat ggcgagcatg    780
gtgctgtacg aagcgaacat cctgggcgtc atgtctgaag tgctgagtgc tgtttttgcg    840
gaagtcatga acggtaaacc ggaatttacc gatcatctga cgcacaaact gaaacatcac    900
ccgggccaga ttgaagcagc tgcgatcatg gaacatattc tggatggcag cggttatgtt    960
aaagccgcag aactgctgca cgaaatggat ccgctgcaga aaccgaaaca agaccgttat   1020
gcactgcgta ccagcccgca gtggctgggt ccgcaaattg aagtgatccg ttctgcgacg   1080
aaaatgatcg aacgcgaaat taattctgtg aacgataatc cgctgatcga cgttagtcgt   1140
aacaaagcac tgcatggcgg taattttcag ggcaccccga ttggtgttgc tatggataac   1200
acgcgcctgg cgattgctgc gatcggcaaa ctgctgtttg cgcaattcag tgaactggtg   1260
aatgactatt acaacaatgg cctgccgtcc aacctgaccg gttcccgtga tccgtcactg   1320
gactatggct ttaagggtgc ggaaattgcc atggcatcgt actgcagcga actgcagttc   1380
ctggccaacc cggtgaccaa tcatgttcaa tccgcagaac agcacaacca agatgtcaat   1440
tcactgggtc tgatctcatc gcgcaaaacg tcggaagcgg tggaaattct gaaactgatg   1500
agctctagtt tcctggtggc cctgtgtcag gcagttgatc tgcgtcatat cgaagaaaat   1560
gtccgcctgg ctgtgaagaa aaccgtcagt caagtggcga agaaaaccct gaacattggc   1620
gttgatggtg tcctgcaccc gtctcgtttt agtgaaaaag aactgctgcg tgtcgtggac   1680
cgcgaatatg tgttcgctta cgcggatgac ccgtgctccg cgacctatcc gctgatgcag   1740
aaactgcgcg aagtgctggt ttctcatgcc ctggcaaaca gtggcaatga aaaagatgcc   1800
tccacctcaa tctttcacaa aattggcgtt ttcgaagaag aactgaaagg tatcctgccg   1860
aaagaagttg aaaacgctcg tgcgtcagtc gaaaatggta ccccggccat cccgaacaaa   1920
attgaagaat gccgttcgta tccgctgtac aaatttgtgc gcggcgaact gggtaccgaa   1980
ctgctgacgg gcgaaaaagt ccgcagcccg ggtgaagaac tggatcaggt gttcaatgcg   2040
ctgtgcgaag gcaaactggt tgacccgctg ctggcttgtc tggaagcctg gaatggtgcc   2100
ccgctgccga tttgttaa                                                 2118
```

<210> SEQ ID NO 3
<211> LENGTH: 705
<212> TYPE: PRT
<213> ORGANISM: Lithospermum erythrorhizon
<220> FEATURE:
<223> OTHER INFORMATION: LiePAL Polypeptide

<400> SEQUENCE: 3

```
Met Glu Asn Gly Asn Gly Lys Met Glu Phe Cys Met Lys Asp Pro Leu
1               5                   10                  15

Asn Trp Gly Met Ala Ala Glu Ser Met Lys Gly Ser His Leu Asp Glu
            20                  25                  30

Val Lys Lys Met Val Ala Glu Phe Arg Lys Pro Val Val Gln Leu Ala
        35                  40                  45

Gly Lys Thr Leu Thr Ile Ala Gln Val Ala Ala Ile Ala Ala Arg Asp
    50                  55                  60

Asp Gly Val Thr Val Glu Leu Ala Glu Ala Ala Arg Glu Gly Val Lys
65                  70                  75                  80

Ala Ser Ser Asp Trp Val Met Glu Ser Met Asn Lys Gly Thr Asp Ser
                85                  90                  95

Tyr Gly Val Thr Thr Gly Phe Gly Ala Thr Ser His Arg Arg Thr Lys
            100                 105                 110

Gln Gly Gly Ala Leu Gln Lys Glu Leu Ile Arg Phe Leu Asn Ala Gly
        115                 120                 125

Ile Phe Gly Asn Gly Thr Glu Thr Ser His Thr Leu Pro His Ser Ala
    130                 135                 140

Thr Arg Ala Ala Met Leu Val Arg Ile Asn Thr Leu Leu Gln Gly Tyr
145                 150                 155                 160

Ser Gly Ile Arg Phe Glu Ile Leu Glu Ala Ile Thr Lys Phe Leu Asn
                165                 170                 175

Thr Asn Ile Thr Pro Cys Leu Pro Leu Arg Gly Thr Ile Thr Ala Ser
            180                 185                 190

Gly Asp Leu Val Pro Leu Ser Tyr Ile Ala Gly Leu Leu Thr Gly Arg
        195                 200                 205

Pro Asn Ser Lys Ala Val Gly Pro Thr Gly Glu Lys Leu Asn Ala Glu
    210                 215                 220

Glu Ala Phe Arg Leu Ala Gly Ile Ser Ser Gly Phe Phe Glu Leu Gln
225                 230                 235                 240

Pro Lys Glu Gly Leu Ala Leu Val Asn Gly Thr Ala Val Gly Ser Gly
                245                 250                 255

Met Ala Ser Met Val Leu Tyr Glu Ala Asn Ile Leu Gly Val Met Ser
            260                 265                 270

Glu Val Leu Ser Ala Val Phe Ala Glu Val Met Asn Gly Lys Pro Glu
        275                 280                 285

Phe Thr Asp His Leu Thr His Lys Leu Lys His His Pro Gly Gln Ile
    290                 295                 300

Glu Ala Ala Ala Ile Met Glu His Ile Leu Asp Gly Ser Gly Tyr Val
305                 310                 315                 320

Lys Ala Ala Glu Leu Leu His Glu Met Asp Pro Leu Gln Lys Pro Lys
                325                 330                 335

Gln Asp Arg Tyr Ala Leu Arg Thr Ser Pro Gln Trp Leu Gly Pro Gln
            340                 345                 350

Ile Glu Val Ile Arg Ser Ala Thr Lys Met Ile Glu Arg Glu Ile Asn
        355                 360                 365

Ser Val Asn Asp Asn Pro Leu Ile Asp Val Ser Arg Asn Lys Ala Leu
```

-continued

```
    370                 375                 380

His Gly Gly Asn Phe Gln Gly Thr Pro Ile Gly Val Ala Met Asp Asn
385                 390                 395                 400

Thr Arg Leu Ala Ile Ala Ala Ile Gly Lys Leu Leu Phe Ala Gln Phe
                405                 410                 415

Ser Glu Leu Val Asn Asp Tyr Tyr Asn Asn Gly Leu Pro Ser Asn Leu
            420                 425                 430

Thr Gly Ser Arg Asp Pro Ser Leu Asp Tyr Gly Phe Lys Gly Ala Glu
        435                 440                 445

Ile Ala Met Ala Ser Tyr Cys Ser Glu Leu Gln Phe Leu Ala Asn Pro
    450                 455                 460

Val Thr Asn His Val Gln Ser Ala Glu Gln His Asn Gln Asp Val Asn
465                 470                 475                 480

Ser Leu Gly Leu Ile Ser Ser Arg Lys Thr Ser Glu Ala Val Glu Ile
                485                 490                 495

Leu Lys Leu Met Ser Ser Ser Phe Leu Val Ala Leu Cys Gln Ala Val
            500                 505                 510

Asp Leu Arg His Ile Glu Glu Asn Val Arg Leu Ala Val Lys Lys Thr
        515                 520                 525

Val Ser Gln Val Ala Lys Lys Thr Leu Asn Ile Gly Val Asp Gly Val
    530                 535                 540

Leu His Pro Ser Arg Phe Ser Glu Lys Glu Leu Leu Arg Val Val Asp
545                 550                 555                 560

Arg Glu Tyr Val Phe Ala Tyr Ala Asp Asp Pro Cys Ser Ala Thr Tyr
                565                 570                 575

Pro Leu Met Gln Lys Leu Arg Glu Val Leu Val Ser His Ala Leu Ala
            580                 585                 590

Asn Ser Gly Asn Glu Lys Asp Ala Ser Thr Ser Ile Phe His Lys Ile
        595                 600                 605

Gly Val Phe Glu Glu Glu Leu Lys Gly Ile Leu Pro Lys Glu Val Glu
    610                 615                 620

Asn Ala Arg Ala Ser Val Glu Asn Gly Thr Pro Ala Ile Pro Asn Lys
625                 630                 635                 640

Ile Glu Glu Cys Arg Ser Tyr Pro Leu Tyr Lys Phe Val Arg Gly Glu
                645                 650                 655

Leu Gly Thr Glu Leu Leu Thr Gly Glu Lys Val Arg Ser Pro Gly Glu
            660                 665                 670

Glu Leu Asp Gln Val Phe Asn Ala Leu Cys Glu Gly Lys Leu Val Asp
        675                 680                 685

Pro Leu Leu Ala Cys Leu Glu Ala Trp Asn Gly Ala Pro Leu Pro Ile
    690                 695                 700

Cys
705


<210> SEQ ID NO 4
<211> LENGTH: 2144
<212> TYPE: DNA
<213> ORGANISM: Lithospermum erythrorhizon
<220> FEATURE:
<223> OTHER INFORMATION: LiePAL DNA

<400> SEQUENCE: 4

atgattctac cacggcgatt ggcaatggtg ttggcagtgg cggttccccg ggcttttgcc      60

tgaaagaccc gctgaactgg ggtgtcgccg cggaagccat gaaaggcagt catctggaag     120
```

-continued

```
aagttaaggg tatggtcgaa gaatttcgta aaccggtggt tcgcctgggc ggtgaaaccc    180
tgacgatcag tcaggttgca gctattgcag tccgtggctc cgaagttgct gtcgaactgt    240
cagaatcggc ccgcgaaggt gtgaaagcaa gctctgattg ggttatggaa agcatgaata    300
aaggtaccga ctcttatggc gttaccacgg gttttggcgc gaccagccat cgtcgcacga    360
aagaaggcgg tgccctgcag aaagaactga tccgttttct gaatgcaggt attttcggta    420
acggcaccga aagttgccat accctgccgc agagcgcaac ccgtgccgca atgctggtgc    480
gcattaatac gctgctgcaa ggttattcgg gcattcgttt tgaaatcctg gaagccatta    540
gcaaattcct gaacaataac atcaccccgt gtctgccgct gcgcggtacc attacggctt    600
caggcgatct ggtgccgctg tcgtacatcg caggtctgct gaccggccgt cataacagca    660
aagcggttgg tccgacgggc gaaattctgc acccgaaaga agctttccgt ctggcgggcg    720
tggaaggcgg ctttttcgaa ctgcagccga aagaaggtct ggctctggtg aatggtaccg    780
ccgttggtag tggtctggca tccatggttc tgttcgaagc caacatcctg gcagtgctgt    840
cagaagttct gtcggctatt tttgcggaag tgatgcaggg taaaccggaa tttaccgatc    900
atctgacgca caaactgaaa catcacccgg gccaaatcga agcagctgcg atcatggaac    960
atattctgga cggtagttcc tatgttaaag ccgcacagaa actgcacgaa atggatccgc   1020
tgcagaaacc gaaacaagac cgttatgccc tgcgtaccag cccgcaatgg ctgggcccgc   1080
tgattgaagt gatccgttca tcgacgaaaa gcatcgaacg cgaaattaat tctgtcaatg   1140
ataacccgct gattaatgtg tctcgtaaca aagcgctgca tggcggtaat tttcagggta   1200
ccccgatcgg cgtttcaatg gataacacgc gcctggctgt cgcgtcgatt ggcaaactga   1260
tgtttgccca gttcagcgaa ctggtgaacg atttctataa taacggtctg ccgtcaaatc   1320
tgtcgggcgg tcgtaacccg tctctggact atggttttaa aggcgccgaa attgcaatgg   1380
ctgcgtactg cagtgaactg cagttcctgg caaatccggt caccaaccat gtgcaatctg   1440
ctgaacagca caatcaagat gtcaacagtc tgggtctgat cagctctcgc aaaaccgccg   1500
aagcagtgga cattctgaaa ctgatgagtt ccacgtatct ggttgctctg tgtcaggcgg   1560
tcgatctgcg tcattttgaa gaaaatctgc gcaacaccgt gaaaagcacg gtctctcaag   1620
tggcgaaacg tgtcctgacc atgggtgtga acggcgaact gcacccgagc cgcttttgcg   1680
aaaaagatct gctgcgtgtc gtggaccgcg aatatatctt cgcgtacatt gatgacccgt   1740
gttccgccac ctacccgctg atgcagaaac tgcgccaagt gctggttgaa cacgccctga   1800
aaaatggcga atcagagaaa aacctgagca cctctatctt tcagaaaatt cgtgcattcg   1860
aagaagaaat caaaaccctg ctgccgaaag aagttgaatc cacgcgcgcc gcaattgaaa   1920
atggtaactc agcgatcccg aatcgtatta aagaatgccg ctcgtatccg ctgtacaaat   1980
ttgtgcgtga agaactgggt accgaactgc tgacgggcga aaaagtgcgc tccccgggcg   2040
aagaatttga taaagttttc accgcgctgt gcaaaggtga aatgatcgat ccgctgatgg   2100
actgtctgaa agaatggaac ggcgccccgc tgccgatttg ttaa                    2144
```

<210> SEQ ID NO 5
<211> LENGTH: 706
<212> TYPE: PRT
<213> ORGANISM: Rhodotorula glutinis
<220> FEATURE:
<223> OTHER INFORMATION: RgPAL Polypeptide

<400> SEQUENCE: 5

Met Ala Pro Ser Val Asp Ser Ile Ala Thr Ser Val Ala Asn Ser Leu

-continued

```
1               5                   10                  15

Ser Asn Gly Leu Ala Gly Asp Leu Arg Lys Lys Thr Ser Gly Ala Gly
            20                  25                  30

Ser Leu Leu Pro Thr Thr Glu Thr Thr Gln Ile Asp Ile Val Glu Arg
        35                  40                  45

Ile Leu Ala Asp Ala Gly Ala Thr Asp Gln Ile Lys Leu Asp Gly Tyr
    50                  55                  60

Thr Leu Thr Leu Gly Asp Val Val Gly Ala Ala Arg Arg Gly Arg Thr
65                  70                  75                  80

Val Lys Val Ala Asp Ser Pro Gln Ile Arg Glu Lys Ile Asp Ala Ser
                85                  90                  95

Val Glu Phe Leu Arg Thr Gln Leu Asp Asn Ser Val Tyr Gly Val Thr
            100                 105                 110

Thr Gly Phe Gly Gly Ser Ala Asp Thr Arg Thr Glu Asp Ala Ile Ser
        115                 120                 125

Leu Gln Lys Ala Leu Leu Glu His Gln Leu Cys Gly Val Leu Pro Thr
    130                 135                 140

Ser Met Asp Gly Phe Ala Leu Gly Arg Gly Leu Glu Asn Ser Leu Pro
145                 150                 155                 160

Leu Glu Val Val Arg Gly Ala Met Thr Ile Arg Val Asn Ser Leu Thr
                165                 170                 175

Arg Gly His Ser Ala Val Arg Ile Val Val Leu Glu Ala Leu Thr Asn
            180                 185                 190

Phe Leu Asn His Gly Ile Thr Pro Ile Val Pro Leu Arg Gly Thr Ile
        195                 200                 205

Ser Ala Ser Gly Asp Leu Ser Pro Leu Ser Tyr Ile Ala Ala Ser Ile
    210                 215                 220

Thr Gly His Pro Asp Ser Lys Val His Val Asp Gly Gln Ile Met Ser
225                 230                 235                 240

Ala Gln Glu Ala Ile Ala Leu Lys Gly Leu Gln Pro Val Val Leu Gly
                245                 250                 255

Pro Lys Glu Gly Leu Gly Leu Val Asn Gly Thr Ala Val Ser Ala Ser
            260                 265                 270

Met Ala Thr Leu Ala Leu Thr Asp Ala His Val Leu Ser Leu Leu Ala
        275                 280                 285

Gln Ala Asn Thr Ala Leu Thr Val Glu Ala Met Val Gly His Ala Gly
    290                 295                 300

Ser Phe His Pro Phe Leu His Asp Val Thr Arg Pro His Pro Thr Gln
305                 310                 315                 320

Ile Glu Val Ala Arg Asn Ile Arg Thr Leu Leu Glu Gly Ser Lys Tyr
                325                 330                 335

Ala Val His His Glu Thr Glu Val Lys Val Lys Asp Asp Glu Gly Ile
            340                 345                 350

Leu Arg Gln Asp Arg Tyr Pro Leu Arg Cys Ser Pro Gln Trp Leu Gly
        355                 360                 365

Pro Leu Val Ser Asp Met Ile His Ala His Ser Val Leu Ser Leu Glu
    370                 375                 380

Ala Gly Gln Ser Thr Thr Asp Asn Pro Leu Ile Asp Leu Glu Asn Lys
385                 390                 395                 400

Met Thr His His Gly Gly Ala Phe Met Ala Ser Ser Val Gly Asn Thr
                405                 410                 415

Met Glu Lys Thr Arg Leu Ala Val Ala Leu Met Gly Lys Val Ser Phe
            420                 425                 430
```

```
Thr Gln Leu Thr Glu Met Leu Asn Ala Gly Met Asn Arg Ala Leu Pro
        435                 440                 445

Ser Cys Leu Ala Ala Glu Asp Pro Ser Leu Ser Tyr His Cys Lys Gly
    450                 455                 460

Leu Asp Ile Ala Ala Ala Ala Tyr Thr Ser Glu Leu Gly His Leu Ala
465                 470                 475                 480

Asn Pro Val Ser Thr His Val Gln Pro Ala Glu Met Gly Asn Gln Ala
                485                 490                 495

Ile Asn Ser Leu Ala Leu Ile Ser Ala Arg Arg Thr Ala Glu Ala Asn
            500                 505                 510

Asp Val Leu Ser Leu Leu Leu Ala Thr His Leu Tyr Cys Val Leu Gln
        515                 520                 525

Ala Val Asp Leu Arg Ala Met Glu Phe Glu His Thr Lys Glu Phe Glu
    530                 535                 540

Pro Met Val Thr Asp Leu Leu Lys Gln His Phe Gly Ala Leu Ala Thr
545                 550                 555                 560

Ala Asp Val Glu Asp Lys Val Arg Lys Ser Ile Tyr Lys Arg Leu Gln
                565                 570                 575

Gln Asn Asn Ser Tyr Asp Leu Glu Gln Arg Trp His Asp Thr Phe Ser
            580                 585                 590

Val Ala Thr Gly Ala Val Val Glu Ala Leu Ala Gly Asn Glu Val Ser
        595                 600                 605

Leu Ala Ser Leu Asn Ala Trp Lys Val Ala Cys Ala Glu Lys Ala Ile
    610                 615                 620

Ala Leu Thr Arg Thr Val Arg Asp Ser Phe Trp Ala Ala Pro Ser Ser
625                 630                 635                 640

Ala Ser Pro Ala Leu Lys Tyr Leu Ser Pro Arg Thr Arg Ile Leu Tyr
                645                 650                 655

Ser Phe Val Arg Glu Asp Val Gly Val Lys Ala Arg Arg Gly Asp Val
            660                 665                 670

Tyr Leu Gly Lys Gln Glu Val Thr Ile Gly Thr Asn Val Ser Arg Ile
        675                 680                 685

Tyr Glu Ala Ile Lys Asp Gly Arg Ile Ala Pro Val Leu Val Lys Met
    690                 695                 700

Met Ala
705
```

<210> SEQ ID NO 6
<211> LENGTH: 2121
<212> TYPE: DNA
<213> ORGANISM: Rhodotorula glutinis
<220> FEATURE:
<223> OTHER INFORMATION: RgPAL DNA

<400> SEQUENCE: 6

```
atggccccct ccgtcgactc gatcgcgact tcggtcgcca actcgctctc gaacggactc      60

gccggcgacc tccgcaagaa gacttcgggt gctggctccc tgctgccgac caccgagact     120

acccagatcg acatcgtcga gcgcatcttg gccgacgccg gcgcgacgga ccagatcaaa     180

ctcgacgggt ataccctcac cctcggcgac gtcgtcggcg ccgcccgccg cggccgcacc     240

gtcaaggtcg ccgatagccc ccagattcgc gagaagatcg atgccagtgt cgagttcctc     300

cgcacccagc ttgacaacag tgtctacggt gtcacgaccg gcttcggcgg ctcggcagac     360

acccggacgg aggacgcgat ctcgctgcag aaggctctgc tcgagcacca actctgcggt     420
```

-continued

```
gtcctgccca cctcgatgga cgggttcgcg ctcggacgtg gcctcgagaa ctcgctcccg    480

ctcgaggttg ttcgtggcgc gatgacgatc cgtgtcaact cgctcacgcg cggccactcg    540

gcggtccgca tcgtcgtcct cgaagccctc accaacttcc tcaaccacgg catcaccccg    600

atcgtccccc tccgcggcac catctcggca tcgggtgacc tttccccccct ctcgtacatc    660

gccgcctcga tcaccggtca cccagactcg aaggtgcacg tcgacggcca aatcatgtcc    720

gcccaggagg cgatcgctct caagggtctc caacctgtcg tcctcggtcc gaaggagggt    780

ctcgggctcg tcaacggcac cgccgtctcc gcgtccatgg ccactctcgc cctcaccgac    840

gcgcatgtcc tctcgttgct cgcccaggcc aacacggccc tgaccgtcga ggccatggtc    900

ggacacgccg gctcgttcca cccgttcctg cacgatgtca ctcgcccgca cccgacccag    960

atcgaggtcg cgcgcaacat taggacgctc ctcgagggca gcaagtacgc cgtccaccat   1020

gagaccgagg tcaaggtcaa ggacgacgag ggcatcctcc ggcaggaccg atacccgctc   1080

cgctgctcgc cccagtggct cgggcctctt gtcagtgaca tgatccacgc ccactcggtc   1140

ctctccctcg aggcgggtca gtcgaccacc gacaaccccc tgatcgacct cgagaacaag   1200

atgacccacc acggtggcgc cttcatggcg agcagcgtcg gtaacaccat ggagaagact   1260

cgtctcgccg tcgcacttat gggcaaggtt agcttcactc agctcaccga gatgctcaac   1320

gccggcatga accgcgcgct tccctcctgc ctcgccgccg aggacccgtc tctgtcctac   1380

cactgcaagg gtctcgacat cgccgccgct gcatacactt cggagctcgg tcacctcgcg   1440

aacccagtct cgacccacgt tcagccggca gagatgggca atcaggcgat caactcgctc   1500

gccctcatct cggcccgtcg caccgccgag gcgaacgacg tcctctcgct cctcctcgcc   1560

acccacctct actgcgtctt gcaggcggtc gacctgcgcg cgatggagtt cgagcacacg   1620

aaagagtttg agccgatggt caccgacttg ctcaagcagc actttggcgc gctcgcgaca   1680

gccgacgtcg aggacaaggt ccgcaaatcg atctacaagc ggctgcagca gaacaactcg   1740

tacgacctcg agcagcggtg gcacgacacg ttctcggtcg cgaccggcgc cgtcgtcgaa   1800

gccctcgccg ggaacgaggt gtcgctcgcg agcctgaacg cctggaaggt cgcgtgcgct   1860

gagaaggcca tcgccctgac ccgcaccgtg cgcgactcgt tctgggccgc gccgtcgtcg   1920

gcgtcgcccg cgctcaagta cctctcgccg cggactcgca tcctgtactc gttcgtccgg   1980

gaagacgtcg gcgtcaaggc ccgccgcggc gacgtctacc tcggcaagca ggaggtcacg   2040

atcgggacca acgtcagccg catctacgag gcgatcaagg acggccgcat tgctccggtc   2100

ctcgtcaaga tgatggcata a                                             2121


<210> SEQ ID NO 7
<211> LENGTH: 193
<212> TYPE: PRT
<213> ORGANISM: Saccharomyces cerevisiae
<220> FEATURE:
<223> OTHER INFORMATION: scFrm2 Polypeptide

<400> SEQUENCE: 7

Met Ser Pro Thr Gly Asn Tyr Leu Asn Ala Ile Thr Asn Arg Arg Thr
1               5                   10                  15

Ile Tyr Asn Leu Lys Pro Glu Leu Pro Gln Gly Val Gly Leu Asp Asp
            20                  25                  30

Val Lys Arg Thr Val His Val Ile Leu Lys Asn Thr Pro Thr Ala Phe
        35                  40                  45

Asn Ser Gln Val Asn Arg Ala Val Ile Ile Val Gly Asp Thr His Lys
    50                  55                  60
```

```
Arg Ile Trp Asp Ala Val Ala Ser Ala Met Pro Thr Ala Glu Ala Lys
65                  70                  75                  80

Lys Arg Pro Glu Ser Cys Arg Asp Glu Ala Tyr Gly Ser Val Ile Phe
                85                  90                  95

Phe Thr Asp Glu Gly Pro Thr Glu Lys Leu Gln Arg Asp Phe Pro Ala
            100                 105                 110

Leu Ala Ala Ala Phe Pro Thr Cys Ala Ala His Thr Thr Gly Ala Val
        115                 120                 125

Gln Ile Gln Ser Trp Thr Ala Leu Glu Leu Leu Gly Leu Gly Ala Asn
    130                 135                 140

Leu Gln His Tyr Asn Asp Tyr Val Lys Ser Ala Leu Pro Gln Asp Val
145                 150                 155                 160

Pro Ile Ala Trp Thr Val Gln Ser Gln Leu Val Phe Gly Val Pro Thr
                165                 170                 175

Ala Leu Pro Glu Glu Lys Thr Phe Ile Asn Asn Val Ile Asn Val Tyr
            180                 185                 190

His
```

<210> SEQ ID NO 8
<211> LENGTH: 582
<212> TYPE: DNA
<213> ORGANISM: Saccharomyces cerevisiae
<220> FEATURE:
<223> OTHER INFORMATION: scFrm2 DNA

<400> SEQUENCE: 8

```
atgtccccaa ctggaaacta cttaaacgct attacaaacc gtcgtaccat ctacaatttg     60

aagcccgaat taccacaagg tgtcggtttg gatgatgtaa agagaactgt acacgttatt    120

ctcaagaata cgccaacagc ttttaactca caagtgaatc gcgctgtcat tatcgttggt    180

gatacacaca aaaggatatg ggatgctgtt gcgagcgcaa tgccaactgc tgaagccaag    240

aagagaccag agtcttgcag agatgaggct tacggttcag tcattttctt cactgatgaa    300

ggaccaactg aaaaactgca aagagatttt ccagccttgg cagccgcttt cccaacatgc    360

gccgctcata cgaccggtgc tgtgcaaatt cagtcttgga ctgccctcga actattggga    420

ttgggggcta atttgcaaca ctataatgac tacgtcaaat ctgctttgcc tcaagatgtt    480

cctattgcgt ggactgtaca atctcaattg gtctttggtg ttccaactgc cttgccagaa    540

gaaaagactt ttatcaataa cgtaatcaac gtttatcact ga                       582
```

<210> SEQ ID NO 9
<211> LENGTH: 193
<212> TYPE: PRT
<213> ORGANISM: Saccharomyces cerevisiae
<220> FEATURE:
<223> OTHER INFORMATION: scHbn1 Polypeptide

<400> SEQUENCE: 9

```
Met Ser Ala Val Ala Thr Tyr Leu Lys Thr Leu Thr Ala Arg Arg Thr
1               5                   10                  15

Ile Tyr Ala Leu Lys Pro Glu Leu Pro Gly Glu Ile Thr Ile Asn Asp
            20                  25                  30

Ile Gln Ser Val Val Gln Thr Ile Ile Lys Glu Thr Pro Thr Ala Phe
        35                  40                  45

Asn Ser Gln Pro Asn Arg Ala Val Ile Leu Thr Gly Glu Thr His Lys
    50                  55                  60
```

Lys Val Trp Asp Glu Val Thr Lys Ala Ile Glu Ser Pro Ala Gly Gln
65 70 75 80

Lys Arg Pro Ala Ser Ala Arg Asp Glu Ala Phe Gly Ser Val Ile Phe
85 90 95

Phe Thr Asp Asp Lys Val Thr Glu Lys Leu Lys Ala Asp Phe Pro Ala
100 105 110

Tyr Ala Ala Ala Phe Pro Ser Phe Ala Asp His Thr Ser Gly Ala Ala
115 120 125

Gln Ile Asn Ser Trp Val Ala Leu Glu Ala Met Gly Leu Gly Gly His
130 135 140

Leu Gln His Tyr Asn Gly Tyr Ile Lys Ala Ala Leu Pro Ser Lys Ile
145 150 155 160

Pro Glu Ser Trp Thr Val Gln Ala Gln Leu Val Phe Gly Thr Pro Ala
165 170 175

Ala Pro Pro Gly Glu Lys Thr Tyr Ile Lys Asn Asp Val Glu Ile Phe
180 185 190

Asn

<210> SEQ ID NO 10
<211> LENGTH: 582
<212> TYPE: DNA
<213> ORGANISM: Saccharomyces cerevisiae
<220> FEATURE:
<223> OTHER INFORMATION: scHbn1 DNA

<400> SEQUENCE: 10
atgtctgctg ttgcaactta tttgaaaact ttaactgctc gtcgtactat ttacgctttg 60
aaaccggagt tacctggtga aattactatc aacgacatcc aatccgtcgt ccaaaccatc 120
attaaagaaa cacccaccgc tttcaactcc cagccaaatc gcgctgttat cttgactggt 180
gaaactcaca aaaaagtttg ggacgaagtg actaaggcta tagaaagccc tgccggtcaa 240
aagaggcctg cttcagcaag ggatgaggcc tttggttctg taatcttctt caccgacgac 300
aaggtaactg aaaagctaaa ggctgacttc ccagcgtacg cagctgcatt ccctagtttc 360
gcggaccata cctctggtgc cgctcaaatc aactcgtggg ttgccttgga ggcaatgggc 420
ctgggtggtc acctacaaca ctacaatggt tacataaaag ctgctttgcc aagcaaaatc 480
cctgagtctt ggaccgtaca agctcaatta gtcttcggta ccccagccgc acctccaggt 540
gaaaagacct acatcaaaaa cgatgttgaa atcttcaatt aa 582

<210> SEQ ID NO 11
<211> LENGTH: 640
<212> TYPE: PRT
<213> ORGANISM: Clostridium difficile
<220> FEATURE:
<223> OTHER INFORMATION: cdFLDZ Polypeptide

<400> SEQUENCE: 11

Met Lys Ile Ser Ser Met Phe Thr Pro Ile Arg Ile Gly Ser Met Thr
1 5 10 15

Val Pro Asn Arg Phe Val Val Pro Pro Met Gly Asn Asn Phe Ala Asn
20 25 30

Thr Asp Gly Thr Leu Ser Glu Thr Ser Lys Ala Tyr Tyr Leu Glu Arg
35 40 45

Ala Leu Gly Gly Phe Gly Leu Ile Thr Ile Glu Ser Ser Val Val Asp
50 55 60

Lys Lys Ala Lys Gly Gly Pro Arg Lys Pro Cys Leu Tyr Asp Asp Ser

```
65                  70                  75                  80

Thr Ile Asp Ser Phe Lys Asn Val Ile Asp Ala Cys His Asp Ala Gly
                85                  90                  95

Ser Lys Val Ser Ile Gln Leu Gln His Ala Gly Ser Glu Gly Asn Glu
            100                 105                 110

Lys Val Ala Gly His Pro Leu Lys Ala Ala Ser Ala Ile Pro Ala Ser
        115                 120                 125

Asn Gly Arg Asn Thr Pro Leu Ala Ile Thr Thr Glu Glu Ile Tyr Glu
    130                 135                 140

Leu Ile Glu Ser Tyr Gly Asp Ala Ala Leu Arg Ala Gln Lys Ala Gly
145                 150                 155                 160

Ala Asp Ala Val Glu Val His Cys Ala His Gly Tyr Leu Val Ser Ser
                165                 170                 175

Phe Ile Ser Gln Arg Thr Asn Lys Arg Val Asp Glu Phe Gly Gly Cys
            180                 185                 190

Phe Glu Asn Arg Met Arg Leu Pro Arg Leu Ile Ile Glu Asn Ile Arg
        195                 200                 205

Lys Lys Val Gly Asn Ser Leu Ala Ile Leu Cys Arg Ile Asn Ser Thr
    210                 215                 220

Asp Asp Val Pro Gly Gly Ile Asp Val His Asp Ser Ser Val Ile Ala
225                 230                 235                 240

Ala Tyr Leu Glu Asp Cys Gly Ile Asp Gly Leu His Val Ser Arg Ser
                245                 250                 255

Ile His Ile His Asp Glu Tyr Met Trp Ala Pro Thr Thr Leu His Ala
            260                 265                 270

Gly Phe Ser Ala Glu Leu Val Thr Glu Ile Lys Lys Ala Val Ser Ile
        275                 280                 285

Pro Val Ile Thr Val Gly Arg Tyr Thr Glu Pro Gln Phe Ala Glu Leu
    290                 295                 300

Met Val Arg Gln Gly Arg Cys Asp Leu Val Ala Phe Gly Arg Gln Ser
305                 310                 315                 320

Leu Ala Asp Pro Glu Met Pro Asn Lys Ala Lys Asn Gly Lys Leu Asp
                325                 330                 335

Glu Met Ile Pro Cys Ile Ala Cys Leu Gln Gly Cys Val Pro Asn Met
            340                 345                 350

Phe Gln Gly Lys Pro Ile Ala Cys Leu Ala Asn Pro Ile Leu Gly His
        355                 360                 365

Glu Ala Glu Leu Lys Pro Ala Glu Ile Ser Lys Glu Val Leu Val Val
    370                 375                 380

Gly Gly Gly Val Gly Gly Met Leu Ala Ala Trp Val Cys Ala Lys Arg
385                 390                 395                 400

Gly His Asn Val Thr Leu Val Glu Lys Ser Glu Val Leu Gly Gly Gln
                405                 410                 415

Met Arg Leu Ala Ala Tyr Pro Pro Gly Lys Gly Asp Ile Thr Asn Leu
            420                 425                 430

Val Arg Ser Tyr Ile Ser Lys Cys Asn Gln Tyr Gly Val Lys Ile Cys
        435                 440                 445

Thr Asn Thr Glu Ala Thr Val Glu Leu Ile Lys Glu Lys Ser Pro Asp
    450                 455                 460

Val Val Ile Ile Ala Thr Gly Ala Thr Pro Leu Val Leu Pro Ile Pro
465                 470                 475                 480

Gly Ile Asn Asp Ser Gly Leu Ile His Ala Val Asp Leu Leu Asp Gly
                485                 490                 495
```

-continued

```
Lys Lys Ser Cys Gly Lys Lys Val Leu Val Val Gly Gly Gly Met Val
            500                 505                 510

Gly Cys Glu Val Ala Ala Phe Leu Gly Glu Gln Glu His Glu Val Thr
        515                 520                 525

Val Ile Glu Leu Arg Glu Glu Val Gly Ala Asp Val Ile Ser Glu His
    530                 535                 540

Arg Lys Phe Leu Met Asn Asp Phe Glu Asn Tyr Asn Ile His Thr Ile
545                 550                 555                 560

Thr Gly Ala Lys Val Ser Lys Phe Tyr Asp Asp Gly Val Asp Tyr Leu
                565                 570                 575

Leu Thr Asp Gly Thr Glu His Asp Leu Lys Gly Phe Asp Ser Val Val
            580                 585                 590

Leu Ala Met Gly Ser Arg Asn Tyr Asp Pro Leu Ser Glu Val Ile Lys
        595                 600                 605

Glu Val Val Lys Glu Thr Tyr Ile Val Gly Asp Ala Val Lys Ala Arg
    610                 615                 620

Arg Ala Leu Asp Ala Thr Lys Glu Ala Phe Glu Val Ala Leu Asn Ile
625                 630                 635                 640
```

<210> SEQ ID NO 12
<211> LENGTH: 1923
<212> TYPE: DNA
<213> ORGANISM: Clostridium difficile
<220> FEATURE:
<223> OTHER INFORMATION: cdFLDZ DNA

<400> SEQUENCE: 12

```
atgaagatta gttctatgtt tacacctata agaattggtt caatgacagt tccaaatcgt     60

tttgtagttc cccctatggg aaacaatttt gcaaacacag atggtacttt aagtgaaact    120

tctaaggctt attatcttga gcgtgcttta ggtggttttg gattaataac tatagaatct    180

agtgttgtag acaaaaaagc aaaaggaggt cctcgtaagc cttgtttata tgatgatagc    240

acaatagata gttttaaaaa tgtaatagat gcttgtcatg atgcaggttc gaaggtatct    300

atacaattac aacatgctgg ttctgaagga aatgaaaaag tagcaggaca tccattaaaa    360

gctgcttctg caatacctgc atcaaatggt cgtaatacac cactagcaat aacaacagaa    420

gaaatatatg aacttataga atcttatgga gatgctgcat tacgtgcaca aaaagctggt    480

gcagatgctg ttgaagttca ctgcgctcat ggatatctgg ttagtagttt tatatcacaa    540

agaacaaata agcgtgtaga tgagtttggt ggatgttttg aaaatagaat gagattacct    600

cgtcttatca ttgaaaatat acgtaaaaaa gtaggaaatt ctctagcaat attatgtcgt    660

ataaacagta ctgatgatgt tccaggagga attgatgtac acgatagttc agtaatagca    720

gcatatctag aagattgtgg aatagatgga cttcatgttt cacgtagtat acatatacat    780

gatgaatata tgtgggctcc tacgacttta catgctggat tcagtgcaga attagttact    840

gaaataaaaa aagctgttag tataccagta ataacagttg gacgttatac agagccacag    900

tttgctgagt taatggtcag acaaggaaga tgtgatttag tagcattcgg tagacaaagc    960

ttggctgacc cagaaatgcc taataaagct aaaaatggaa aactagacga aatgatacca   1020

tgtattgcat gcttacaagg atgtgtacca aatatgttcc aaggcaaacc tatagcctgt   1080

cttgcaaatc ctatattagg acatgaagca gagcttaagc cagctgaaat tagcaaagaa   1140

gttcttgttg ttggtggagg tgttggaggt atgcttgcag catgggtatg tgctaaaaga   1200

ggacataatg taactttagt tgaaaaatct gaagttcttg gtgggcaaat gcgtttagct   1260
```

```
gcatatcctc caggaaaagg agatattact aacttagtta gaagttatat ttcaaaatgt   1320

aatcaatatg gtgtaaaaat atgtactaat acagaagcta cagtagaact tataaaagag   1380

aaatcacctg atgtagttat tatagctact ggagcaactc cacttgtact tcctatacca   1440

ggaatcaatg attcaggatt aattcatgct gtagaccttc ttgatggtaa aaaatcttgt   1500

gggaaaaaag tacttgttgt tggaggtgga atggttggat gtgaagtggc agccttcctt   1560

ggagaacaag aacatgaggt tactgttatt gagcttagag aagaagttgg tgcagatgta   1620

atttcagaac accgtaaatt ccttatgaat gattttgaaa attataatat acataccatt   1680

actggtgcaa aagtttctaa attttatgat gatggtgtcg actatttact tacagatggc   1740

acagagcatg atttaaaagg ttttgattca gtagtacttg ctatgggttc tcgtaattac   1800

gacccattaa gtgaagttat aaaagaagtt gtaaaagaaa cttatattgt tggtgatgca   1860

gtaaaagctc gtagggcatt agatgcaaca aaagaagctt ttgaagtagc attaaatata   1920

taa                                                                 1923
```

```
<210> SEQ ID NO 13
<211> LENGTH: 240
<212> TYPE: PRT
<213> ORGANISM: Escherichia coli
<220> FEATURE:
<223> OTHER INFORMATION: nfsA Polypeptide

<400> SEQUENCE: 13

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Ser Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Arg Pro Phe Ile Leu Asp Tyr Leu His Lys Gln Gly Trp Ala Thr Arg
225                 230                 235                 240
```

<210> SEQ ID NO 14
<211> LENGTH: 723
<212> TYPE: DNA
<213> ORGANISM: Escherichia coli
<220> FEATURE:
<223> OTHER INFORMATION: nfsA DNA

<400> SEQUENCE: 14
atgacgccaa ccattgaact tatttgtggc catcgctcca ttcgccattt cactgatgaa 60
cccatttccg aagcgcagcg tgaggcgatt attaacagcg cccgtgcgac gtccagttcc 120 agtttttgc agtgcagtag cattattcgc attaccgaca aagcgttacg tgaagaactg 180
gtgacgctga ccggcgggca aaaacacgta gcgcaagcgg cggagttctg ggtgttctgt 240
gccgacttta accgccattt acagatctgt ccggatgctc agctcggcct ggcggaacaa 300
ctgttgctcg gtgtcgttga tacggcaatg atggcgcaga atgcattaat cgcagcggaa 360
tcgctgggat tgggcggggt atatatcggc ggcctgcgca ataatattga agcggtgacg 420
aaactgctta aattaccgca gcatgttctg ccgctgtttg ggctgtgcct tggctggcct 480
gcggataatc cggatcttaa gccgcgttta ccggcctcca ttttggtgca tgaaaacagc 540
tatcaaccgc tggataaagg cgcactggcg cagtatgacg agcaactggc ggaatattac 600
ctcacccgtg gcagcaataa tcgccgggat acctggagcg atcatatccg ccgaacaatc 660
attaaagaaa gccgcccatt tattctggat tatttgcaca aacagggttg ggcgacgcgc 720
taa 723

<210> SEQ ID NO 15
<211> LENGTH: 217
<212> TYPE: PRT
<213> ORGANISM: Escherichia coli
<220> FEATURE:
<223> OTHER INFORMATION: nfsB Polypeptide

<400> SEQUENCE: 15

Met Asp Ile Ile Ser Val Ala Leu Lys Arg His Ser Thr Lys Ala Phe
1 5 10 15

Asp Ala Ser Lys Lys Leu Thr Pro Glu Gln Ala Glu Gln Ile Lys Thr
20 25 30

Leu Leu Gln Tyr Ser Pro Ser Ser Thr Asn Ser Gln Pro Trp His Phe
35 40 45

Ile Val Ala Ser Thr Glu Glu Gly Lys Ala Arg Val Ala Lys Ser Ala
50 55 60

Ala Gly Asn Tyr Val Phe Asn Glu Arg Lys Met Leu Asp Ala Ser His
65 70 75 80

Val Val Val Phe Cys Ala Lys Thr Ala Met Asp Asp Val Trp Leu Lys
85 90 95

Leu Val Val Asp Gln Glu Asp Ala Asp Gly Arg Phe Ala Thr Pro Glu
100 105 110

Ala Lys Ala Ala Asn Asp Lys Gly Arg Lys Phe Phe Ala Asp Met His
115 120 125

Arg Lys Asp Leu His Asp Asp Ala Glu Trp Met Ala Lys Gln Val Tyr
130 135 140

Leu Asn Val Gly Asn Phe Leu Leu Gly Val Ala Ala Leu Gly Leu Asp
145 150 155 160

Ala Val Pro Ile Glu Gly Phe Asp Ala Ala Ile Leu Asp Ala Glu Phe
165 170 175

-continued

```
Gly Leu Lys Glu Lys Gly Tyr Thr Ser Leu Val Val Val Pro Val Gly
            180                 185                 190

His His Ser Val Glu Asp Phe Asn Ala Thr Leu Pro Lys Ser Arg Leu
        195                 200                 205

Pro Gln Asn Ile Thr Leu Thr Glu Val
    210                 215


<210> SEQ ID NO 16
<211> LENGTH: 654
<212> TYPE: DNA
<213> ORGANISM: Escherichia coli
<220> FEATURE:
<223> OTHER INFORMATION: nfsB DNA

<400> SEQUENCE: 16

atggatatca tttctgtcgc cttaaagcgt cattccacta aggcatttga tgccagcaaa     60

aaacttaccc cggaacaggc cgagcagatc aaaacgctac tgcaatacag cccatccagc    120

accaactccc agccgtggca ttttattgtt gccagcacgg aagaaggtaa agcgcgtgtt    180

gccaaatccg ctgccggtaa ttacgtgttc aacgagcgta aaatgcttga tgcctcgcac    240

gtcgtggtgt tctgtgcaaa aaccgcgatg gacgatgtct ggctgaagct ggttgttgac    300

caggaagatg ccgatggccg ctttgccacg ccggaagcga aagccgcgaa cgataaaggt    360

cgcaagttct tcgctgatat gcaccgtaaa gatctgcatg atgatgcaga gtggatggca    420

aaacaggttt atctcaacgt cggtaacttc ctgctcggcg tggcggctct gggtctggac    480

gcggtaccca tcgaaggttt tgacgccgcc atcctcgatg cagaatttgg tctgaaagag    540

aaaggctaca ccagtctggt ggttgttccg gtaggtcatc acagcgttga agattttaac    600

gctacgctgc cgaaatctcg tctgccgcaa aacatcacct taaccgaagt gtaa          654


<210> SEQ ID NO 17
<211> LENGTH: 28
<212> TYPE: DNA
<213> ORGANISM: Artificial Sequence
<220> FEATURE:
<223> OTHER INFORMATION: scFrm2 Primer 5'

<400> SEQUENCE: 17

aacggatccg atgtccccaa ctggaaac                                        28


<210> SEQ ID NO 18
<211> LENGTH: 30
<212> TYPE: DNA
<213> ORGANISM: Artificial Sequence
<220> FEATURE:
<223> OTHER INFORMATION: scFrm2 Primer 3'

<400> SEQUENCE: 18

gccaagcttc agtgataaac gttgattacg                                      30


<210> SEQ ID NO 19
<211> LENGTH: 27
<212> TYPE: DNA
<213> ORGANISM: Artificial Sequence
<220> FEATURE:
<223> OTHER INFORMATION: scHbn1 Primer 5'

<400> SEQUENCE: 19

aacggatccg atgtctgctg ttgcaac                                         27
```

<210> SEQ ID NO 20
<211> LENGTH: 29
<212> TYPE: DNA
<213> ORGANISM: Artificial Sequence
<220> FEATURE:
<223> OTHER INFORMATION: scHbn1 Primer 3'

<400> SEQUENCE: 20
gccaagctta attgaagatt tcaacatcg 29

<210> SEQ ID NO 21
<211> LENGTH: 28
<212> TYPE: DNA
<213> ORGANISM: Artificial Sequence
<220> FEATURE:
<223> OTHER INFORMATION: cdFLDZ Primer 5'

<400> SEQUENCE: 21
ccgggatcca atgaagatta gttctatg 28

<210> SEQ ID NO 22
<211> LENGTH: 27
<212> TYPE: DNA
<213> ORGANISM: Artificial Sequence
<220> FEATURE:
<223> OTHER INFORMATION: cdFLDZ Primer 3'

<400> SEQUENCE: 22
ccggaattct tatatattta atgctac 27

<210> SEQ ID NO 23
<211> LENGTH: 37
<212> TYPE: DNA
<213> ORGANISM: Artificial Sequence
<220> FEATURE:
<223> OTHER INFORMATION: nfsA primer 5'

<400> SEQUENCE: 23
cagaccatgg gcacgccaac cattgaactt atttgtg 37

<210> SEQ ID NO 24
<211> LENGTH: 29
<212> TYPE: DNA
<213> ORGANISM: Artificial Sequence
<220> FEATURE:
<223> OTHER INFORMATION: nfsA primer 3'

<400> SEQUENCE: 24
gaggatcctt agcgcgtcgc ccaaccctg 29

<210> SEQ ID NO 25
<211> LENGTH: 30
<212> TYPE: DNA
<213> ORGANISM: Artificial Sequence
<220> FEATURE:
<223> OTHER INFORMATION: nfsB primer 5'

<400> SEQUENCE: 25
cagaccatgg gcgatatcat ttctgtcgcc 30

<210> SEQ ID NO 26
<211> LENGTH: 30
<212> TYPE: DNA
<213> ORGANISM: Artificial Sequence
<220> FEATURE:
<223> OTHER INFORMATION: nfsB primer 3'

-continued

<400> SEQUENCE: 26
gaggatcctt acacttcggt taaggtgatg 30